US 11,213,351 B2

(12) United States Patent
Yu et al.

(10) Patent No.: US 11,213,351 B2
(45) Date of Patent: Jan. 4, 2022

(54) SURGICAL LASER SYSTEMS AND LASER DEVICES

(71) Applicant: Boston Scientific Scimed, Inc., Maple Grove, MN (US)

(72) Inventors: Honggang Yu, San Jose, CA (US); Rongwei Jason Xuan, Fremont, CA (US); Jian James Zhang, Santa Clara, CA (US); David N. Horn, San Jose, CA (US); Xirong Yang, Fremont, CA (US); Thomas Hasenberg, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 330 days.

(21) Appl. No.: 16/251,278

(22) Filed: Jan. 18, 2019

(65) Prior Publication Data

US 2019/0151022 A1  May 23, 2019

Related U.S. Application Data

(63) Continuation of application No. 14/940,323, filed on Nov. 13, 2015, now Pat. No. 10,219,863.

(Continued)

(51) Int. Cl.
*A61B 18/24* (2006.01)
*A61B 18/20* (2006.01)
(Continued)

(52) U.S. Cl.
CPC .......... *A61B 18/24* (2013.01); *A61B 1/0638* (2013.01); *A61B 18/20* (2013.01); *A61B 18/22* (2013.01);
(Continued)

(58) Field of Classification Search
None
See application file for complete search history.

(56) References Cited

U.S. PATENT DOCUMENTS

| 3,590,248 A | * | 6/1971 | Chatterton, Jr. ..... | G02B 6/4249 398/91 |
| 4,089,584 A | * | 5/1978 | Polczynski .......... | G02B 6/2804 385/123 |

(Continued)

FOREIGN PATENT DOCUMENTS

| CN | 102131545 A | 7/2011 |
| CN | 103018823 A | 12/2012 |

(Continued)

OTHER PUBLICATIONS

Merriam-Webster, definition of "bundle", retrieved from www.merriam-webster.com/dictionary/bundle on Mar. 28, 2014.

(Continued)

*Primary Examiner* — Carl H Layno
*Assistant Examiner* — Manolis Pahakis
(74) *Attorney, Agent, or Firm* — Bookoff McAndrews, PLLC

(57) ABSTRACT

A surgical laser system includes an array of laser diodes that are configured to output laser energy, a fiber bundle, a delivery fiber, and a tubular sheath. The fiber bundle includes a plurality of optical fibers and has a proximal end that is configured to receive laser energy from the array of laser diodes. The delivery fiber includes a proximal end that is configured to receive laser energy from a distal end of the fiber bundle. The tubular sheath defines a lumen, in which at least a portion of the delivery fiber is disposed. The tubular sheath is insertable into a working channel of an endoscope or a cystoscope. A distal end of the tubular sheath is (Continued)

configured to deliver laser energy discharged from the delivery fiber into a body of a patient.

17 Claims, 23 Drawing Sheets

Related U.S. Application Data

(60) Provisional application No. 62/079,621, filed on Nov. 14, 2014.

(51) Int. Cl.
*A61B 1/06* (2006.01)
*A61B 18/22* (2006.01)
*A61B 5/00* (2006.01)
*A61B 18/00* (2006.01)

(52) U.S. Cl.
CPC ........... *A61B 5/0075* (2013.01); *A61B 5/0084* (2013.01); *A61B 2018/00172* (2013.01); *A61B 2018/00642* (2013.01); *A61B 2018/00982* (2013.01); *A61B 2018/208* (2013.01); *A61B 2018/2035* (2013.01); *A61B 2018/2065* (2013.01); *A61B 2018/2211* (2013.01); *A61B 2018/2244* (2013.01)

(56) References Cited

U.S. PATENT DOCUMENTS

| | | | | |
|---|---|---|---|---|
| 4,932,747 A * | 6/1990 | Russell | ............... | G02B 6/04 |
| | | | | 219/121.6 |
| 5,268,978 A * | 12/1993 | Po | ............... | G02B 6/2804 |
| | | | | 385/33 |
| 5,363,463 A | 11/1994 | Kleinerman | | |
| 5,373,576 A * | 12/1994 | Minns | ............... | G02B 6/032 |
| | | | | 359/341.3 |
| 5,394,492 A | 2/1995 | Hwang | | |
| 5,513,195 A * | 4/1996 | Opower | ............... | B23K 26/032 |
| | | | | 372/18 |
| 5,668,903 A * | 9/1997 | Neuberger | ............... | G02B 6/2817 |
| | | | | 372/50.1 |
| 5,708,747 A * | 1/1998 | Danckwerth | ............... | G02B 6/403 |
| | | | | 385/115 |
| 5,729,568 A * | 3/1998 | Opower | ............... | B23K 26/032 |
| | | | | 372/108 |
| 5,754,716 A * | 5/1998 | Kim | ............... | A61B 5/1459 |
| | | | | 385/28 |
| 6,011,890 A * | 1/2000 | Neuberger | ............... | G02B 6/04 |
| | | | | 385/121 |
| 6,167,075 A * | 12/2000 | Craig | ............... | H01S 3/094003 |
| | | | | 372/32 |
| 6,201,989 B1 | 3/2001 | Whitehead et al. | | |
| 6,391,022 B1 | 5/2002 | Furumoto et al. | | |
| 6,400,875 B1 | 6/2002 | Lincoln et al. | | |
| 6,519,387 B1 * | 2/2003 | Sunagawa | ............... | G02B 6/4206 |
| | | | | 347/225 |
| 6,882,429 B1 | 4/2005 | Weitekamp et al. | | |
| 7,329,887 B2 * | 2/2008 | Henson | ............... | F21K 9/00 |
| | | | | 250/494.1 |
| 7,456,805 B2 * | 11/2008 | Ouderkirk | ............... | A61C 19/004 |
| | | | | 250/461.1 |
| 7,502,537 B2 * | 3/2009 | Kurahashi | ............... | B23K 1/0056 |
| | | | | 385/115 |
| 8,047,985 B2 * | 11/2011 | Harris | ............... | G02B 21/0076 |
| | | | | 600/108 |
| 8,158,957 B2 * | 4/2012 | Nelson | ............... | G01N 21/55 |
| | | | | 250/458.1 |
| 8,320,724 B2 * | 11/2012 | Sasaoka | ............... | G02B 6/4249 |
| | | | | 385/121 |
| 8,588,267 B1 * | 11/2013 | Panak | ............... | G02B 6/425 |
| | | | | 372/69 |
| 9,599,507 B2 | 3/2017 | Pawluczyk et al. | | |
| 2001/0055462 A1 | 12/2001 | Seibel | | |
| 2002/0097400 A1 | 7/2002 | Jung et al. | | |
| 2002/0138072 A1 | 9/2002 | Black et al. | | |
| 2003/0109787 A1 | 6/2003 | Black | | |
| 2003/0109860 A1 | 6/2003 | Black | | |
| 2003/0214571 A1 * | 11/2003 | Ishikawa | ............... | B23K 26/0604 |
| | | | | 347/255 |
| 2004/0039242 A1 | 2/2004 | Tolkoff et al. | | |
| 2004/0082940 A1 * | 4/2004 | Black | ............... | A61B 18/203 |
| | | | | 606/9 |
| 2004/0150828 A1 * | 8/2004 | Hendrix | ............... | G01N 21/55 |
| | | | | 356/445 |
| 2004/0218635 A1 * | 11/2004 | Schlueter | ............... | H01S 3/06708 |
| | | | | 372/6 |
| 2004/0240489 A1 * | 12/2004 | Teramura | ............... | G02B 27/0994 |
| | | | | 385/38 |
| 2005/0152655 A1 * | 7/2005 | Sunagawa | ............... | C03B 37/01211 |
| | | | | 385/125 |
| 2005/0279354 A1 | 12/2005 | Deutsch et al. | | |
| 2007/0038124 A1 * | 2/2007 | Fulghum, Jr. | ............... | A61B 5/0071 |
| | | | | 600/476 |
| 2007/0041083 A1 * | 2/2007 | Di Teodoro | ............... | G02B 6/02347 |
| | | | | 359/333 |
| 2007/0154153 A1 * | 7/2007 | Fomitchov | ............... | G02B 6/06 |
| | | | | 385/115 |
| 2007/0219601 A1 | 9/2007 | Neuberger | | |
| 2007/0291265 A1 * | 12/2007 | Holman | ............... | G01J 3/10 |
| | | | | 356/320 |
| 2008/0310181 A1 * | 12/2008 | Gurevich | ............... | G02B 6/0006 |
| | | | | 362/554 |
| 2009/0109698 A1 * | 4/2009 | Koyata | ............... | G03B 21/208 |
| | | | | 362/553 |
| 2009/0275927 A1 * | 11/2009 | Fein | ............... | H01S 3/2232 |
| | | | | 606/3 |
| 2010/0228089 A1 | 9/2010 | Hoffman et al. | | |
| 2010/0278503 A1 * | 11/2010 | Nakai | ............... | G02B 6/02033 |
| | | | | 385/142 |
| 2011/0134519 A1 * | 6/2011 | Cooper | ............... | G02B 21/06 |
| | | | | 359/385 |
| 2011/0135260 A1 * | 6/2011 | Nakai | ............... | G02B 6/14 |
| | | | | 385/123 |
| 2011/0196356 A1 * | 8/2011 | Neuberger | ............... | A61B 18/18 |
| | | | | 606/15 |
| 2011/0295347 A1 * | 12/2011 | Wells | ............... | A61N 5/0613 |
| | | | | 607/89 |
| 2012/0010465 A1 | 1/2012 | Erikawa et al. | | |
| 2012/0101374 A1 | 4/2012 | Tearney et al. | | |
| 2012/0232534 A1 | 9/2012 | Rink et al. | | |
| 2012/0307512 A1 | 12/2012 | Cogger et al. | | |
| 2013/0336343 A1 | 12/2013 | Miyabe et al. | | |
| 2014/0071521 A1 * | 3/2014 | Liu | ............... | G02B 6/1228 |
| | | | | 359/341.3 |
| 2014/0078378 A1 * | 3/2014 | Demers | ............... | G02B 6/0005 |
| | | | | 348/359 |
| 2015/0062573 A1 | 3/2015 | Liu et al. | | |
| 2015/0216398 A1 | 8/2015 | Yang et al. | | |
| 2016/0101263 A1 | 4/2016 | Blumenkranz et al. | | |
| 2016/0357007 A1 | 12/2016 | Swanson | | |
| 2016/0363728 A1 | 12/2016 | Wang et al. | | |
| 2017/0071509 A1 | 3/2017 | Pandey et al. | | |
| 2017/0082805 A1 * | 3/2017 | Saikawa | ............... | G02B 6/43 |
| 2017/0224220 A1 | 8/2017 | Tunnell et al. | | |
| 2018/0157039 A1 * | 6/2018 | Yu | ............... | G02B 6/04 |
| 2018/0281108 A1 * | 10/2018 | Victor | ............... | B23K 26/0648 |

FOREIGN PATENT DOCUMENTS

| | | |
|---|---|---|
| EP | 2241280 A2 | 10/2010 |
| JP | H09-173346 A | 12/1995 |

(56) References Cited

FOREIGN PATENT DOCUMENTS

JP       2005-513762         5/2005
WO    WO 2014/074678 A1    5/2014

OTHER PUBLICATIONS

International Search Report and Written Opinion for corresponding International Application No. PCT/US2015/060547, dated Mar. 3, 2016 (9 pages).

* cited by examiner

SURGICAL LASER SYSTEMS AND LASER DEVICES

CROSS REFERENCE TO RELATED APPLICATIONS

This application is a continuation of U.S. patent application Ser. No. 14/940,323, filed Nov. 13, 2015, now U.S. Pat. No. 10,219,863, which is based on and claims the benefit of priority of U.S. Provisional Patent Application No. 62/079,621, filed Nov. 14, 2014, the content of each of which is incorporated by reference herein in its entirety.

BACKGROUND

Embodiments of the invention generally relate to laser devices including, for example, laser systems, laser bars and laser modules comprising laser diodes, and methods of using the laser devices.

Lasers have been increasingly adopted as medical surgical tools and optical fibers have been normally used as delivery devices. As compared to traditional surgical tools, laser surgery can reduce bleeding, pain and infection. Additionally, patients often have less hospitalization time after laser surgery.

High power and high brightness fiber-coupled diode lasers have been increasingly adopted in industrial and medical applications because of their intrinsically simple design, low cost and high wall plug efficiency. Laser diode bars, which comprise multiple laser diodes, have been the common building blocks for the high power laser systems. However, for some wavelength ranges, laser diode bars are not available. Thus, it is necessary to utilize only single semiconductor laser diode emitters or semiconductor lasers (hereinafter "laser diodes") for these wavelength ranges.

Due to their low power, it is necessary to combine the output laser energy from multiple laser diodes into an optical fiber to provide the desired power level. However, it can be difficult to combine the laser energy from individual laser diodes into a single composite beam, particularly when it is desired to have a high power composite laser energy beam (e.g., more than 100 W) using low power (e.g., 1-3 W) laser diodes.

Different surgical applications often utilize laser energy having different properties. For example, different surgical applications may require laser energy having different wavelengths, different pulse widths and pulse repetition rates, different beam sizes and shapes, different power intensities and different feedback systems.

Embodiments of the invention provide solutions to these and other problems.

SUMMARY

Embodiments are directed to surgical laser systems and laser devices utilizing a plurality of laser diodes. One embodiment of a surgical laser system includes an array of laser diodes that are configured to output laser energy, a fiber bundle, a delivery fiber, and a tubular sheath. The fiber bundle includes a plurality of optical fibers and has a proximal end that is configured to receive laser energy from the array of laser diodes. The delivery fiber includes a proximal end that is configured to receive laser energy from a distal end of the fiber bundle. The tubular sheath defines a lumen, in which at least a portion of the delivery fiber is disposed. The tubular sheath is insertable into a working channel of an endoscope or a cystoscope. A distal end of the tubular sheath is configured to deliver laser energy discharged from the delivery fiber into a body of a patient.

Some embodiments are directed to a method of treating a patient using the above-described surgical laser system. In one embodiment of the method, the tubular sheath is inserted into a body of the patient. A first sub-array of the laser diodes are operated to deliver a first beam of laser energy to a tissue of the patient. The first and a second sub-array of the laser diodes are simultaneously operated to deliver a second beam of laser energy to the tissue of the patient having a different size or shape than the first beam.

Another embodiment is directed to a method of producing a laser beam using a surgical laser system. In the method, a discreet beam of laser energy is output from each of a first sub-array of laser diodes. A proximal end of a fiber bundle is optically coupled to the discreet beams of laser energy. The discreet beams of laser energy are discharged through a distal end of the fiber bundle. A proximal end of a delivery fiber is optically coupled to the discreet beams of laser energy discharged through the distal end of the fiber bundle. A composite beam of laser energy comprising the discreet beams of laser energy is discharged through a distal end of the delivery fiber. In some embodiments, the shape of the composite beam is adjusted by outputting discreet beams of laser energy from a second sub-array of the laser diodes that is different from the first sub-array. In some embodiments, the method comprises adjusting a size of the composite beam by outputting discreet beams of laser energy from a second sub-array of the laser diodes that is different from the first sub-array.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
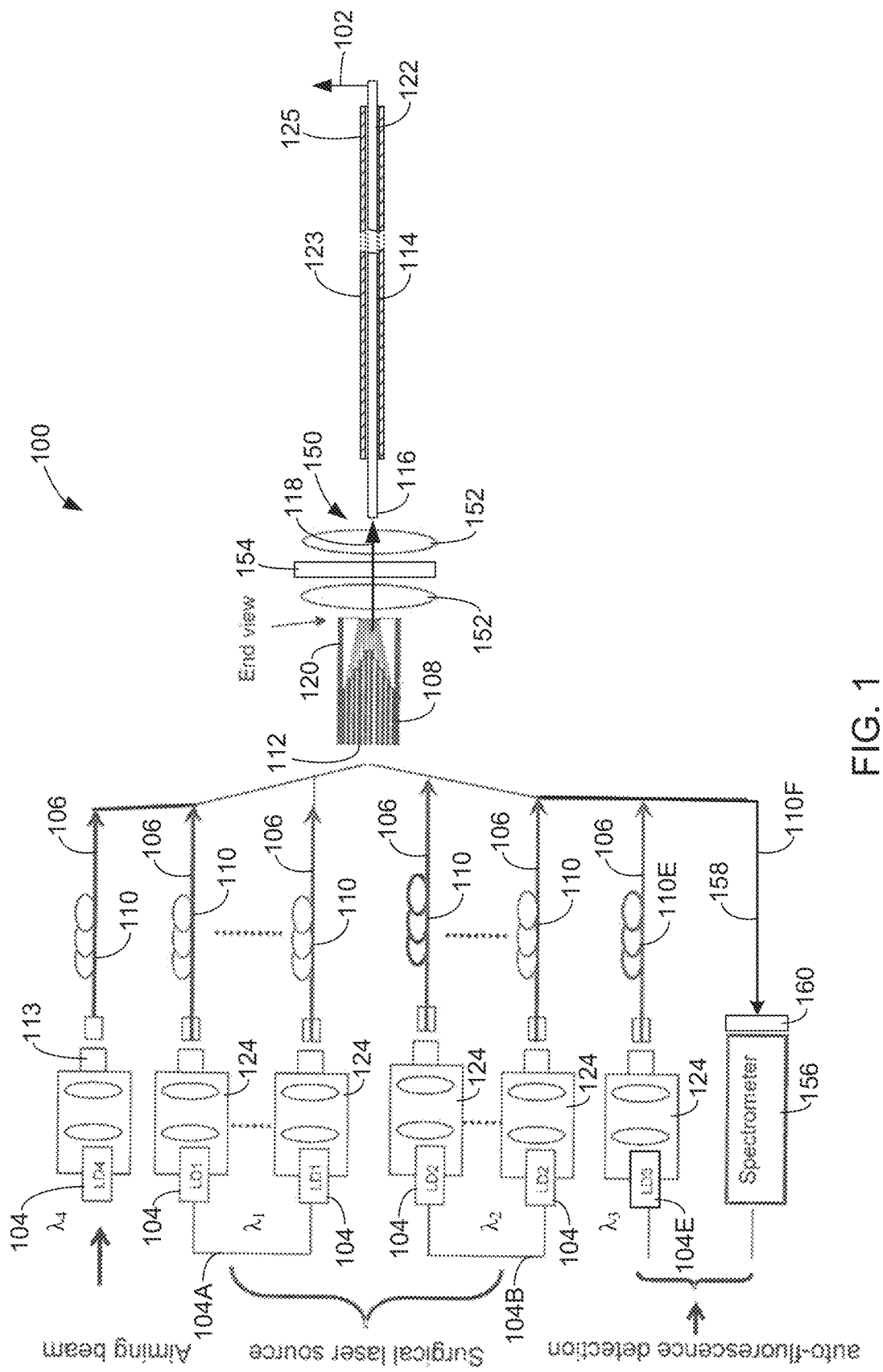
FIG. 1 is a schematic diagram of a laser system in accordance with embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, devices, and/or computer program products, for example. Accordingly, the present invention may take the form of an entirely hardware embodiment, an entirely software embodiment or an embodiment combining software and hardware aspects. The computer program or software aspect of the present invention may comprise computer readable instructions or code stored in a computer readable medium or memory. Execution of the program instructions by one or more processors (e.g., central processing unit) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for example, optical scanning of the paper or other medium, then compiled, interpreted, or otherwise processed in a suitable manner, if necessary, and then stored in a computer memory.

Embodiments of the invention may also be described using flowchart illustrations and block diagrams. Although a flowchart may describe the operations as a sequential process, many of the operations can be performed in parallel or concurrently. In addition, the order of the operations may be re-arranged. A process is terminated when its operations are completed, but could have additional steps not included in a figure or described herein.

It is understood that one or more of the blocks (of the flowcharts and block diagrams) may be implemented by computer program instructions. These program instructions may be provided to a processor circuit, such as a microprocessor, microcontroller or other processor, which executes the instructions to implement the functions specified in the block or blocks through a series of operational steps to be performed by the processor(s) and corresponding hardware components.

FIG. 1 is a schematic diagram of an exemplary laser system 100 in accordance with the embodiments of the invention. In some embodiments, the laser system 100 is configured to operate as a surgical laser system that generates an output beam of laser energy 102 that may be used to perform a surgical laser treatment to tissue of a patient, such as cutting, ablation, coagulation, lithotripsy or other surgical laser treatment.

In some embodiments, the system 100 includes a plurality of laser diodes 104, each of which is configured to output discrete laser energy 106. In some embodiments, the system 100 includes a fiber bundle 108 comprising a plurality of optical fibers 110, as shown in the simplified end or cross-sectional view of the fiber bundle 108 of FIG. 2. The fiber bundle 108 and the optical fibers 110 have a proximal end 112 that is coupled by way of a fiber connector 113 to the laser energy 106 output from the laser diodes 104. In some embodiments, the system 100 includes a delivery fiber 114 having a proximal end 116 that is coupled (i.e., optically coupled) to the laser energy 118 discharged through a distal end 120 of the fiber bundle 108, which comprises the laser energy 106 output from the activated laser diodes 104. In some embodiments, the composite or output laser energy 102, which comprises the laser energy 106 output from the activated laser diodes 104, is discharged through a distal end 122 of the delivery fiber 114.

In some embodiments, the system 100 includes a tubular sheath 123 having a lumen in which the delivery fiber 114 is disposed. In some embodiments, the tubular sheath is insertable into a working channel of an endoscope or cystoscope. A distal end 125 of the tubular sheath 123 is configured to facilitate the delivery of the laser energy 102 discharged from the distal end 122 of the delivery fiber 114 into a body of a patient during a surgical laser treatment.

In some embodiments, the laser energy 106 output from the each of the laser diodes 104 is optically coupled to one or more of the laser fibers 110 of the fiber bundle 108 using suitable optics 124. In some embodiments, at least one of the optical fibers 110 of the fiber bundle 108 is coupled to a subset of the laser diodes 104 of the system 100 (laser diode subset or sub-array) comprising one or more laser diodes 104 using the optics 124. In some embodiments, the optics 124 include one or more optical lenses. In some embodiments, the optical lenses include a single aspheric lens and/or double lenses.

In some embodiments, the optical fibers 110 of the fiber bundle 108 may comprise different fiber subsets, each of which have different fiber properties than the optical fibers 110 of other fiber subsets. The fiber properties of the optical fibers 110 of the fiber bundle 108 may include, for example, a size of a core of the optical fiber 110, a shape of the core of the optical fiber 110, and a numerical aperture of the optical fiber 110. The exemplary fiber bundle 108 shown in FIG. 2 includes three fiber subsets: a first fiber subset comprising optical fibers 110A; a second fiber subset comprising optical fibers 110B; and a third fiber subset comprising the single optical fiber 110C. In this exemplary embodiment, the fiber subsets 110A-110C comprise optical cores of different sizes.

In some embodiments, the laser system 100 is configured to discharge laser energy 102 having different properties in order to accommodate different applications, such as different laser surgery treatments. For example, the laser system 100 may be configured to vary the wavelength, the power level or intensity, the operating mode (e.g., continuous wave or modulated/pulsed), the shape of the beam profile, and/or other properties of the output laser energy 102.

In some embodiments, optics 150 are configured to couple the proximal end 116 of the delivery fiber 114 to the laser energy 118 discharged from the distal end 120 of the fiber bundle 108, as shown in FIG. 1. In some embodiments, the optics 150 comprise one or more lenses 152.

In some embodiments, this variable output laser energy 102 is facilitated using laser diodes 104 having different laser properties. Exemplary embodiments of the laser properties include a wavelength of the laser energy 106 output by the laser diode 104, an intensity level of the laser energy 106 output by the laser diode 104, a pattern of the laser energy 106 output from the laser diode 104, a duty cycle of the laser energy output from the laser diode 104, an operating mode of the laser diode 104, and other laser properties.

In some embodiments, the system 100 includes two or more subsets or sub-arrays of the laser diodes 104 (laser diode subsets), each of which comprises one or more of the laser diodes 104 having the same or similar laser properties. In some embodiments, the laser properties of the one or more laser diodes 104 of each laser diode subset are different from the laser properties of the laser diodes 104 of other laser diode subsets. As a result, each laser diode subset is capable of producing laser energy 106 having unique properties relative to the other laser diode subsets. In some embodiments, the properties of the output laser energy 102 are adjusted through the selective activation and deactivation of one or more of the laser diode subsets.

Different applications of the output laser energy 102, such as different laser surgical treatments, often require the laser energy 102 to cover different wavelength ranges. For example, the laser energy used to ablate tissue in a benign prostatic hyperplasia (BPH) laser treatment may be different from that selected to cut tissue, ablate tissue, vaporize tissue, coagulate blood, or disintegrate kidney or bladder stones. Green or blue laser energy having a wavelength in the range of 300-600 nm, such as 532 nm, could be useful in performing tissue ablation treatments, such as those used to treat BPH, while laser energy having a wavelength of around 2000 nm is useful in lithotripsy treatments to disintegrate kidney or bladder stones.

In some embodiments, the wavelength(s) of the composite laser energy 102 is set based on the activation of one or more laser diode subsets. For example, in some embodiments, a laser diode subset 104A comprising one or more laser diodes 104 (labeled "LD1") are configured to output laser energy 106 having a first wavelength range ($\lambda_1$), while a laser diode subset 104B comprises one or more laser diodes 104 (labeled "LD2") that are configured to output laser energy 106 having a second wavelength range ($\lambda_2$) that is different from the first wavelength range. Other laser diode subsets can also be used to output laser energy 106 having other unique wavelength ranges. The output laser energy 102 can be configured to include the first wavelength range through the activation of the laser diode subset 104A, and the output laser energy 102 can be configured to include the second wavelength range through the activation of the laser diode subset 104B. Thus, the output laser energy 102 can be configured to include one or both of the first and second wavelength ranges of laser energy 106 through the appropriate activation of one or more of the laser diode subsets 104A and 104B.

In one exemplary surgical application, the first laser diode subset 104A may produce laser energy 106 having a wavelength that is strongly absorbed by hemoglobin (e.g., wavelength of 300-600 nm, such as 532 nm) and, thus, can be used to vaporize tissues containing a higher percentage of hemoglobin. The laser diode subset 104B may produce laser energy 106 at a wavelength that is not readily absorbed by hemoglobin and can be used to coagulate tissues and stop bleeding more efficiently. Accordingly, a laser surgical treatment can be performed using the system 100 to initially vaporize targeted tissue by activating the laser diode subset 104A to produce the output laser energy 102 that is strongly absorbed by the hemoglobin within the tissue. The system 100 can then deactivate the laser diode subset 104A and activate the laser diode subset 104B to produce laser energy 102 that is useful in coagulating the tissues and stopping bleeding.

The intensity or power level of the output laser energy 102 can also be adjusted through the selective activation and deactivation of one or more of the laser diode subsets. For example, when each of the laser diode subsets includes one or more laser diodes 104, the activation of a single laser diode subset can produce the output laser energy 102 having a low power. Additional laser diode subsets can be activated to increase the intensity or power level of the output laser energy 102 resulting from an increase in the number of laser diodes 104 that are activated. As a result, the intensity or power level of the output laser energy 102 may be scaled through the activation or deactivation of the laser diode subsets. In general, the power capability of the system 100 is the sum of the power of the laser energy 106 generated by the laser diodes 104 and hence, the laser diode subsets, of the system. Accordingly, relatively low power laser diodes (e.g., 1-3 W) may be used to generate a substantially higher power laser beam 102 when collectively activated.

The laser diodes 104 or the laser diode subsets of the system 100 may also be configured to output distinct patterns of laser energy 106. For example, one or more of laser diodes 104 may be configured to output laser energy 106 having a specific periodic pattern, such as a periodic pattern of varying of an intensity level of the laser energy 106 (e.g., raising and/or lowering the intensity), a periodic pattern of activating and deactivating the output of the laser energy 106, or other periodic pattern.

The laser diodes 104 or the laser diode subsets may also be configured to operate in distinct operating modes. For example, the laser diodes 104 or the laser diode subsets may be configured to operate in a continuous wave (CW) operating mode, a pulsed wave or modulated operating mode, or other conventional operating mode. In some embodiments, the laser diode subsets comprising the laser diodes 104 are configured to operate in a pulsed wave operating mode, where each laser diode subset may be configured to have unique duty cycles. The duty cycle generally operates to control the average power level of the output laser energy 106, however, the frequency of the pulses determined by the duty cycle may also be useful in certain laser surgical treatments, such as laser lithotripsy. As a result, some embodiments of the system 100 include laser diodes 104 or laser diode subsets that operate in unique operating modes and generate laser energy 106 and output laser energy 102 having unique duty cycles.

Figure 3:
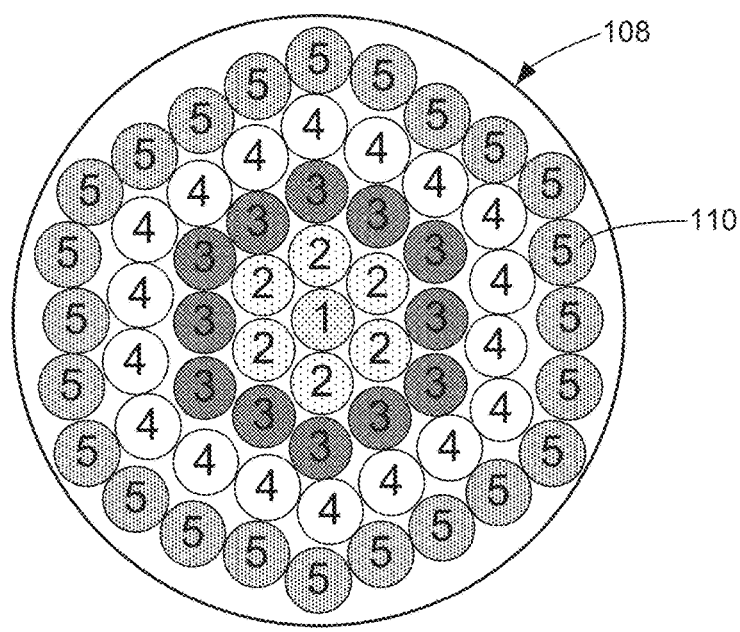
FIG. 3 is a simplified end view of a fiber bundle in accordance with exemplary embodiments of the invention illustrating power intensity scalability.

Accordingly, it is possible to deliver laser energy 106 having different properties through different optical fibers 110 of the optical fiber bundle 108A. FIG. 3 is a simplified end or cross-sectional view of a fiber bundle 108A according to another embodiment of the invention, in which each of the optical fibers 110 has been labeled with a number 1-5 to designate a laser diode subset or sub-array to which they are coupled. That is, the optical fibers 110 that are numbered "4" each are coupled to the laser energy 106 discharged from the laser diodes 104 of one laser diode subset or sub-array, while the optical fibers numbered "5" are each coupled to the laser energy 106 discharged from the laser diodes 104 of another laser diode subset or sub-array. Accordingly, the activation of one or more of the subsets of laser diodes 104 delivers the corresponding laser energy 106 through the corresponding optical fibers 110 and through the delivery fiber 114 as the output laser energy 102.

As a result, the properties of the output laser energy 102 may be customized or tuned through the activation and deactivation of the laser diodes 104 or the laser diode subsets. For example, the system 100 may be operated to activate the laser diode subsets, as indicated by the shaded optical optical fibers 110 (optical fibers 1, 2, 3 and 5), while the laser fiber subset corresponding to the optical fibers 4 is deactivated. This results in composite or output laser energy 102 discharged from the delivery fiber 114 that comprises the laser energy 106 generated by the laser diode subsets corresponding to the optical fibers 1-3 and 5.

Figure 4:
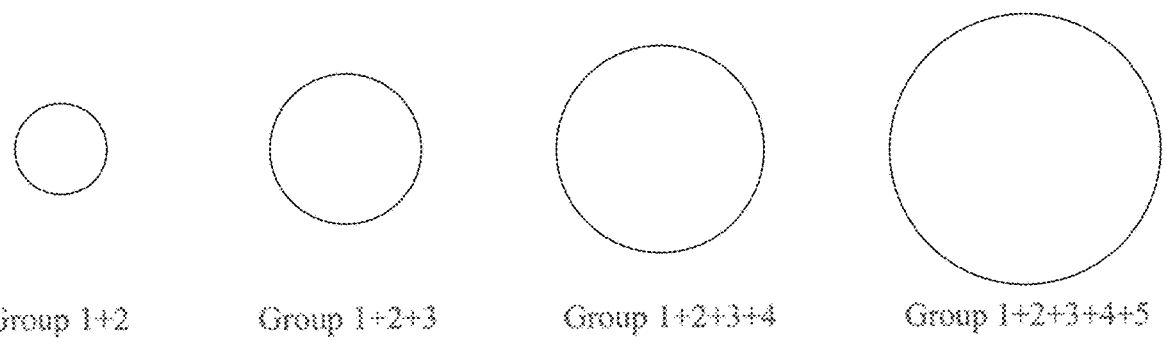
FIG. 4 is a simplified cross-sectional view of an output laser beam that may be produced using the exemplary fiber bundle of FIG. 3.

In some embodiments, the activation and deactivation of different laser diode subsets controls the size of the beam of output laser energy 102 discharged from the laser fiber 114. For example, the laser diode subsets corresponding to the optical fibers 1 and 2 (FIG. 3) may produce an output laser beam 102 having a relatively small diameter, which can be increased by activating other laser diode subsets, such as the laser diode subset corresponding to optical fibers 3-5, as shown in FIG. 4. In some embodiments, when the laser energy 106 output from the laser diodes 104 has substantially the same intensity level, the increase in the size of the diameter of the discharge laser energy 102 maintains a substantially even distribution of the laser energy. The larger diameter beam can be used to remove tissue more quickly while the smaller sized beam can be used to remove tissue more precisely.

In some embodiments, the shape of the output laser beam 102 discharged from the delivery fiber 114 may be chosen or adjusted through the activation of select laser diode subsets and/or the configuration of the delivery fiber 114. In some embodiments, the delivery fiber 114 comprises an optical fiber having a round core, such as a conventional optical fiber, which discharges the laser energy 102 in a circular shaped beam 102.

Figure 5:
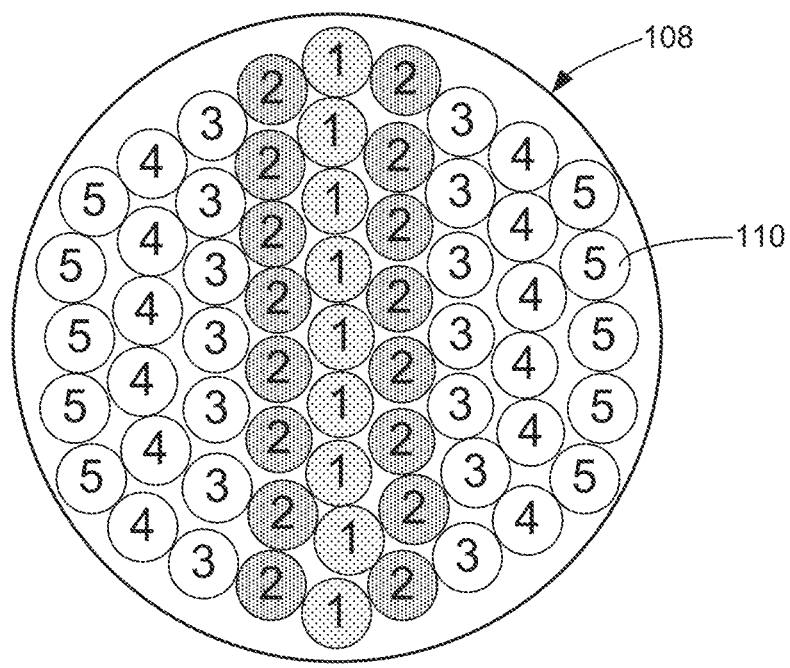
FIG. 5 is a simplified end view of a fiber bundle in accordance with the exemplary embodiments of the invention that illustrates a line shaped beam.
Figure 6:
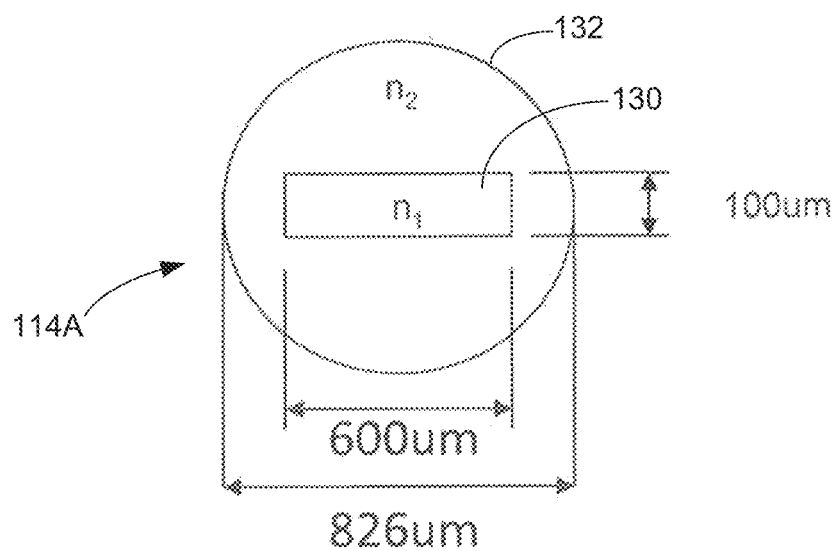
FIG. 6 is a simplified end view of an optical fiber having a rectangular shaped core in accordance with the embodiments of the invention.
Figure 7:
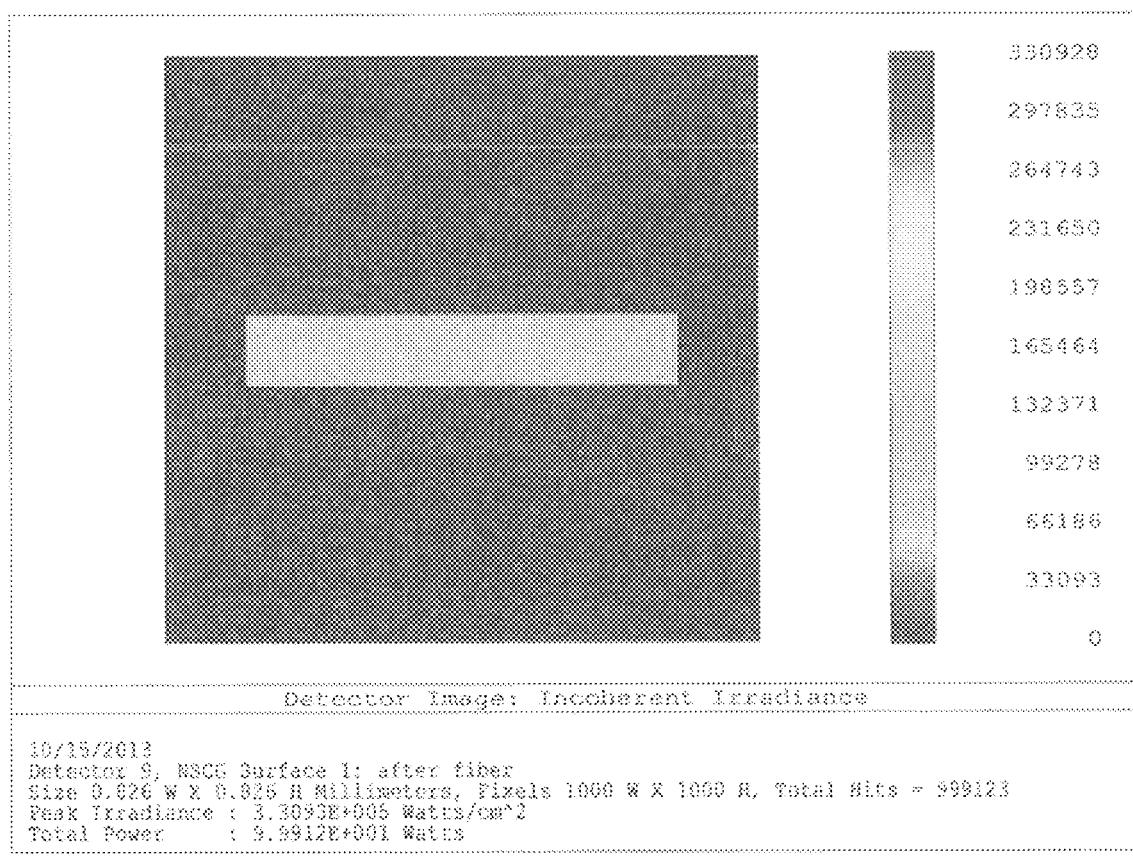
FIG. 7 illustrates a line shaped beam output from the optical fiber of FIG. 6.

FIG. 5 is a simplified end or cross-sectional view of a fiber bundle 108B in accordance with exemplary embodiments of the invention. As illustrated in FIG. 5, the activation of laser diode subsets 1 and 2 deliver laser energy 106 through optical fibers 110 that are oriented in a line. In some embodiments, the delivery fiber 114A comprises an optical fiber having a rectangular core 130 surrounded by cladding 132, as shown in the simplified end or cross-sectional view of FIG. 6. In some embodiments, the index of refraction ($n_1$) of core 130 is greater than the index of refraction ($n_2$) of the cladding 132. The rectangular shaped core 130 allows the delivery fiber 114A to deliver a line shaped output beam 102 to a desired target. FIG. 7 illustrates an exemplary line shaped output beam 102 that may be discharged from the optical fiber of FIG. 6 as simulated using ZEMAX (optical simulation software). In some embodiments, the line shaped laser beam 102 can be used in a surgical laser procedure to enucleate tissues. When the line shaped output beam 102 is swept across tissue, it can also be used to vaporize the tissue more precisely than round shaped laser beams.

Figure 8:
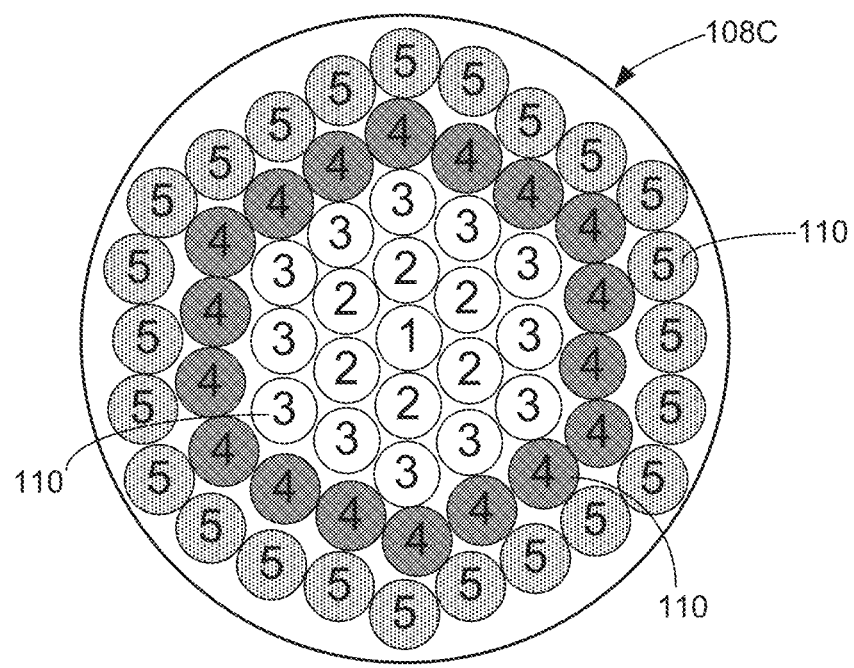
FIG. 8 is a simplified end view of a fiber bundle in accordance with embodiments of the invention illustrating the production of a ring or donut shaped laser beam.

In some embodiments, the system 100 is configured to discharge an annular or donut shaped output beam 102. In some embodiments, this is accomplished by activating laser diode subsets corresponding to optical fibers 110 of the fiber bundle 108C that form an annular or ring pattern. For example, the activation of the laser diode subsets 4 and 5 that deliver laser energy 106 to the corresponding optical fibers 110 of the fiber bundle 108C (FIG. 8) results in a delivery of an annular or donut shaped beam of laser energy 118 to the delivery fiber 114. In some embodiments, the delivery fiber 114 is configured to discharge this annular laser energy as an annular, ring- or donut-shaped beam 102.

Figure 9:
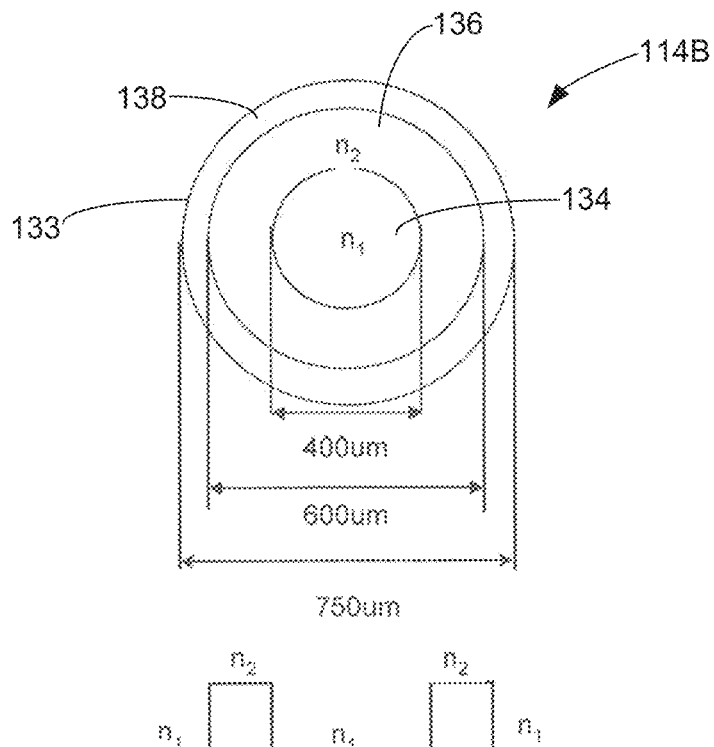
FIG. 9 is a simplified cross-sectional view of a multiple cladding layered optical fiber in accordance with embodiments of the invention.
Figure 10:
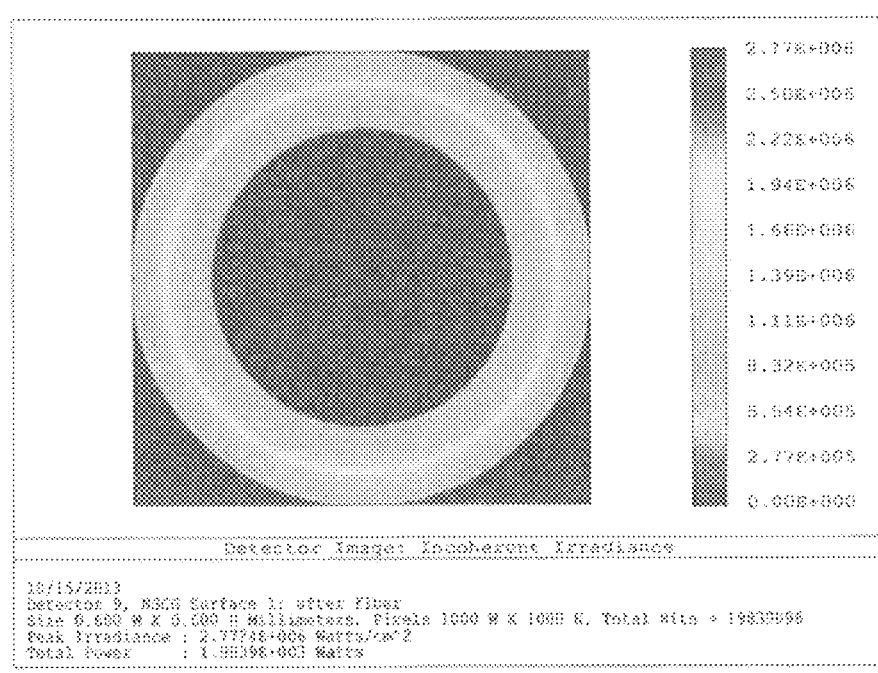
FIG. 10 illustrates a donut or annular shaped laser beam that may be produced using the optical fiber of FIG. 9.

In some embodiments, the delivery fiber 114B may comprise a multiple cladding optical fiber, such as that shown in the simplified cross-sectional view of FIG. 9. In some embodiments, the multiple cladding optical fiber 133 comprises central cladding 134 having an index of refraction ($n_1$) that is lower than the index of refraction ($n_2$) of an annular light delivery medium 136. Additionally, the index of refraction ($n_2$) of the annular light delivery medium 136 is greater than the index of refraction of outer cladding 138. In some embodiments, the annularly shaped energy 106 discharged from the fiber bundle 108C is optically coupled to the annular light delivery medium 136 of the delivery fiber 114B and is discharged through the distal end 122 as an annularly or donut-shaped output beam 102, a simulation of which is illustrated in FIG. 10 using the ZEMAX software. In some embodiments, the annularly shaped output beam 102 is used in a surgical laser procedure to enucleate tissues.

Figure 11:
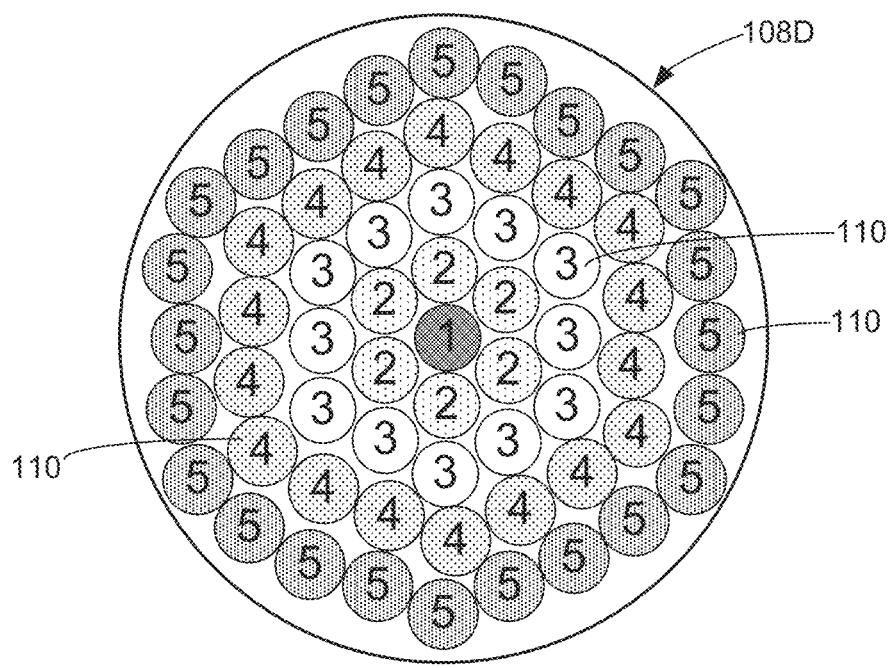
FIG. 11 is a simplified end view of a fiber bundle illustrating optical fibers of the laser bundle carrying beams of laser energy produced by laser diodes having different operating modes.

FIG. 11 is a simplified end or cross-sectional view of a fiber bundle 108D delivering laser energy in accordance with embodiments of the invention. In some embodiments, the laser diode subsets 1, 2, 4 and 5 are activated while the laser diode subset 3 is deactivated. Thus, laser energy 106 generated by the subsets 1, 2, 4 and 5 is delivered through the corresponding optical fibers 110 of the fiber bundle 108D.

Figure 12:
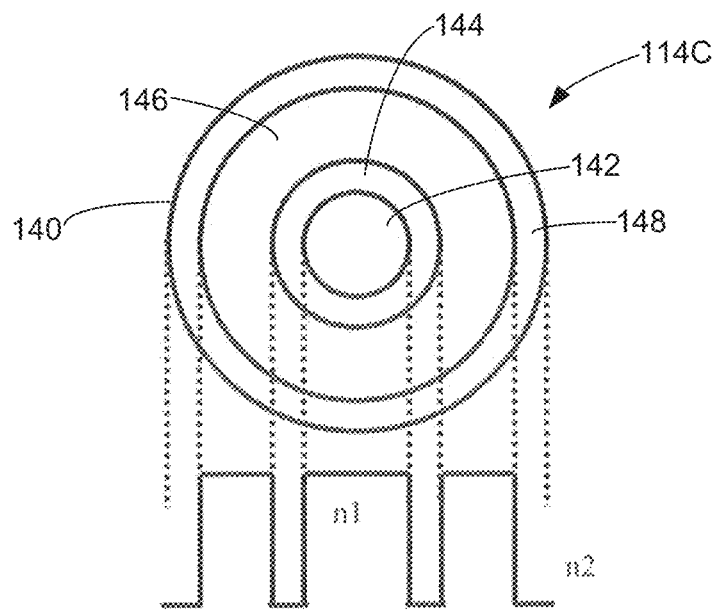
FIG. 12 is a simplified cross-sectional view of an exemplary multiple cladding layered optical fiber in accordance with embodiments of the invention.

In some embodiments, the delivery fiber 114C is a form of a multiple clad fiber 140, a simplified cross-sectional view of which is provided in FIG. 12. In some embodiments, the multiple cladding optical fiber 140 comprises a central light delivery medium 142, a cladding 144, an annular light delivery medium 146 and a cladding 148, as show in FIG. 12. In some embodiments, the central light delivery medium 142 and the annular light delivery medium 146 comprise glass. In some embodiments, the cladding 144 surrounds the central light delivery medium 142 and has an index of refraction ($n_2$) that is less than the index of refraction ($n_1$) of the central light delivery medium 142. The annular light delivery medium 146 surrounds the cladding 144, and the cladding 148 surrounds the annular light delivery medium 146. In some embodiments, the index of refraction ($n_2$) of the cladding 144 and the cladding 148 are less than an index of refraction of the annular light delivery medium 146.

Figure 13:
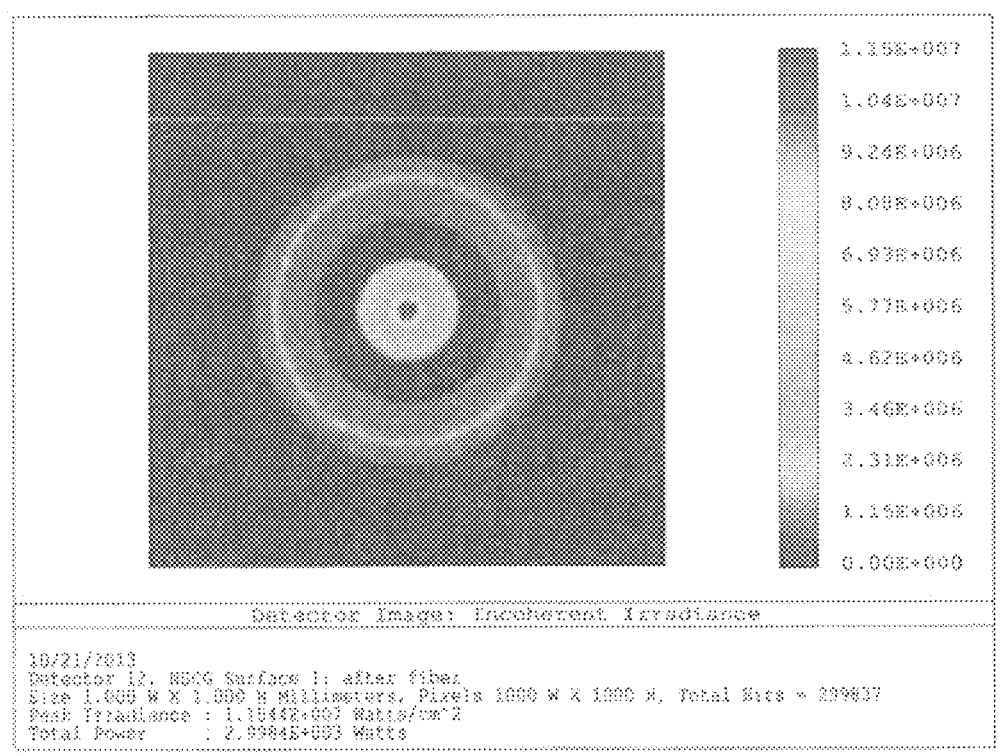
FIG. 13 is illustrated with an exemplary laser beam output from the optical fiber of FIG. 12.

In some embodiments, in order to deliver the laser energy from the embodiment of the fiber bundle 108D depicted in FIG. 11, the delivery fiber 114C depicted in FIG. 12 is used. In this embodiment, the laser energy 106 delivered by the optical fibers 110 of the fiber bundle 108D corresponding to the laser diode subsets 1 and 2 (FIG. 11) is coupled to the central light delivery medium 142, and the laser energy 106 delivered by the optical fibers 110 of the fiber bundle 108D corresponding to the laser diode subsets 4 and 5 is coupled to the annular light delivery medium 146. This configuration allows the delivery fiber 114C to deliver the laser energy 106 in the form of a beam 102 having a central circular portion and an annular portion as illustrated in FIG. 13, which is a simulation produced using the ZEMAX application.

As mentioned above, the laser diodes 104 or the laser diode subsets may be operated to produce laser energy 106 having different properties. For example, one or more laser diode subset may operate in a continuous wave mode or a high duty cycle to produce high intensity or high average power laser energy 106, while other laser diodes 104 or laser diode subsets may be modulated at a certain frequency or duty cycle to produce laser energy 106 having a lower average power or intensity. In some embodiments, the laser diode subsets 1 and 2 (FIG. 11) may be operated in a high powered mode (continuous wave or high duty cycle), while the laser diode subsets 4 and 5 may be modulated to produce a relatively low average power laser energy 106. As a result, the high powered laser energy is centrally located in the fiber bundle 108D while the low powered laser energy is located at the periphery of the fiber bundle 108D. When the delivery fiber 114C of FIG. 12 is used, the high power laser energy 106 is coupled to the central light delivery medium 142, while the lower power laser energy 106 is coupled to the annular light delivery medium 146. The resultant output beam 102 may be used in a surgical procedure in which the central beam cuts or vaporizes tissues while the outer annular beam simultaneously coagulates tissues.

Figure 14:
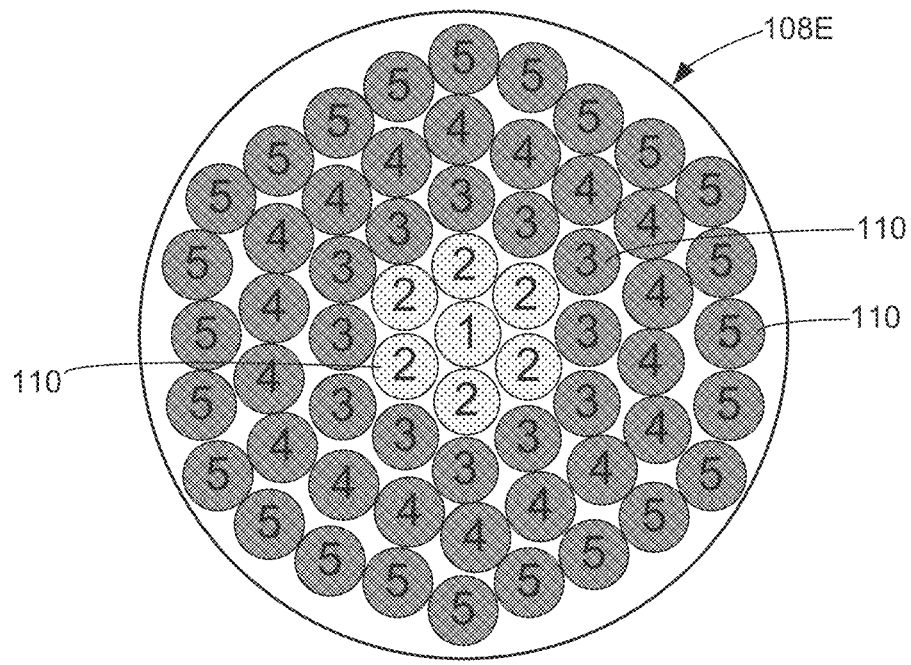
FIG. 14 is a simplified end view of a fiber bundle illustrating the delivery of energy having different wavelengths in accordance with embodiments of the invention.

In some embodiments, the system 100 is configured to deliver laser energy 106 generated by one or more subsets of the laser diodes 104 having a wavelength configured to vaporize tissue, while an inner cluster of the optical fibers 110 are configured to deliver laser energy 106 from one or more subsets of the laser diodes 104 having a wavelength that is configured to coagulate tissue, as shown in FIG. 14, which is a simplified end or cross-sectional view of an exemplary fiber bundle 108E in accordance with embodiments of the invention.

Figure 15:
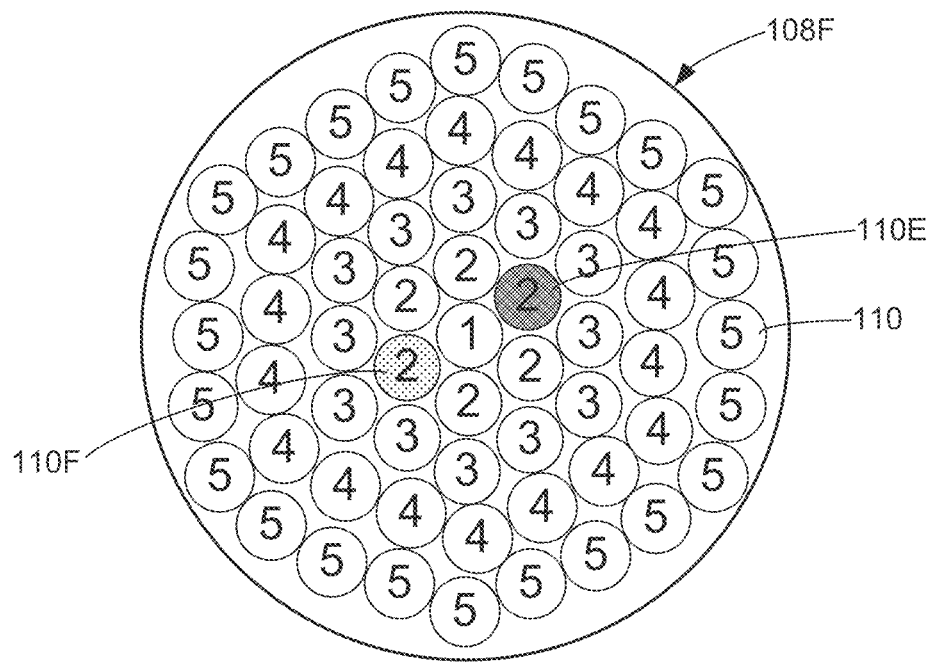
FIG. 15 is a simplified end view of a fiber bundle illustrating laser feedback in accordance with embodiments of the invention.

In some embodiments, the system 100 is configured to provide electromagnetic energy feedback for identification, diagnosis, or other purposes. In some embodiments, the one or more laser diodes 104 include an excitation laser diode 104E (FIG. 1) that is configured to output excitation laser energy 106 having a wavelength in an excitation spectrum, as shown in FIG. 1 and FIG. 14, which is a simplified end or cross-sectional view of the fiber bundle 108E in accordance with embodiments of the invention. The excitation laser energy 106 generated by the laser diode 104E is delivered to a target through at least one of the optical fibers 110 of the fiber bundle 108F, such as laser fiber 110E shown in FIG. 15, and the delivery fiber 114. In some embodiments, the excitation laser energy is combined with laser energy generated from one or more other subsets of the laser diodes 104 and is output as the laser energy 102 from the delivery fiber 114.

In some embodiments, the laser energy generated by the excitation laser diode 104E is transmitted through a band-pass filter 154 (FIG. 1) to ensure that the excitation laser energy is within the desired wavelength range of the excitation spectrum. In some embodiments, the excitation spectrum is in the range of 300-420 nanometers.

In some embodiments, the excitation laser energy is configured to target tissue or other substance that generates auto-fluorescence electromagnetic energy or feedback electromagnetic energy 158 in response to the exposure to the excitation laser energy that can be used to identify the tissue or substance, diagnose a condition of the tissue or substance, or used for other purposes. The feedback electromagnetic energy 158 is captured by the delivery fiber 114 at the distal end 122 and transmitted through the delivery fiber 114 and at least one of the optical fibers 110 of the fiber bundle 108F, such as optical fiber 110F shown in FIG. 15. Co-pending, commonly assigned International Application No. PCT/US14/61319, filed Oct. 20, 2014, the contents of which are incorporated by reference herein in its entirety for all purposes, discloses additional devices and methods to identify conditions at the treatment site.

Figure 2:
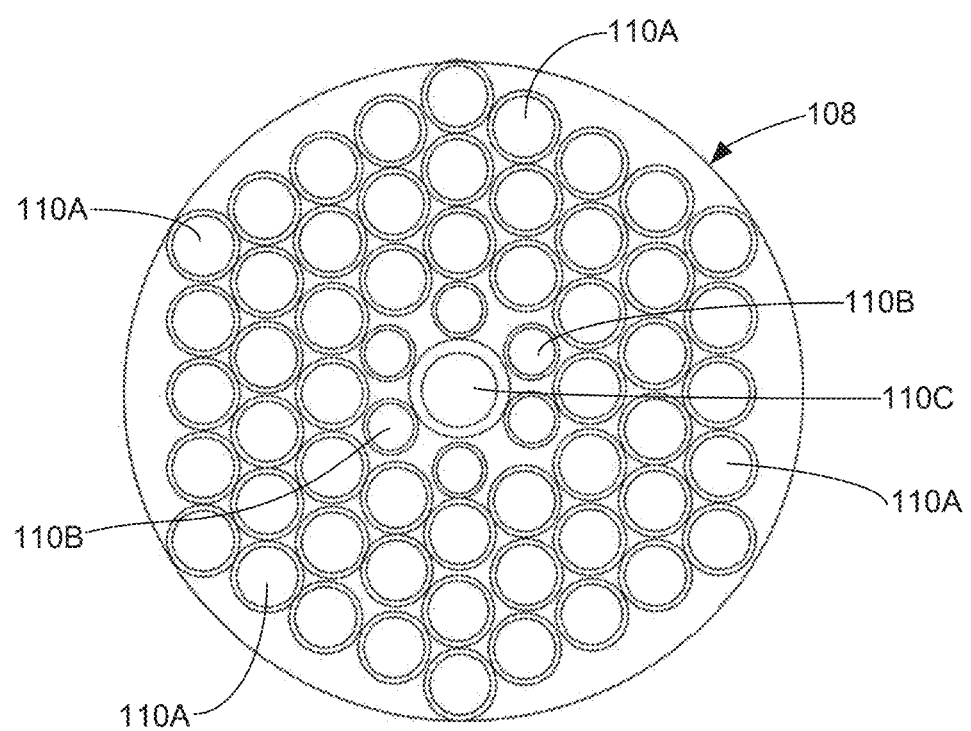
FIG. 2 is a simplified end view of a fiber bundle in accordance with exemplary embodiments of the invention.

In some embodiments, as depicted in FIG. 2, the system 100 includes a spectrometer 156 that is configured to analyze the feedback electromagnetic energy 158. In some embodiments, the system 100 includes a filter 160 that is configured to filter the feedback electromagnetic energy 158, and the filtered feedback electromagnetic energy 158 which is then analyzed by the spectrometer 156. In some embodiments, the filter 160 is configured to remove the excitation spectrum and/or isolate a desired auto-fluorescence spectrum of the feedback electromagnetic energy 158.

Figure 16:
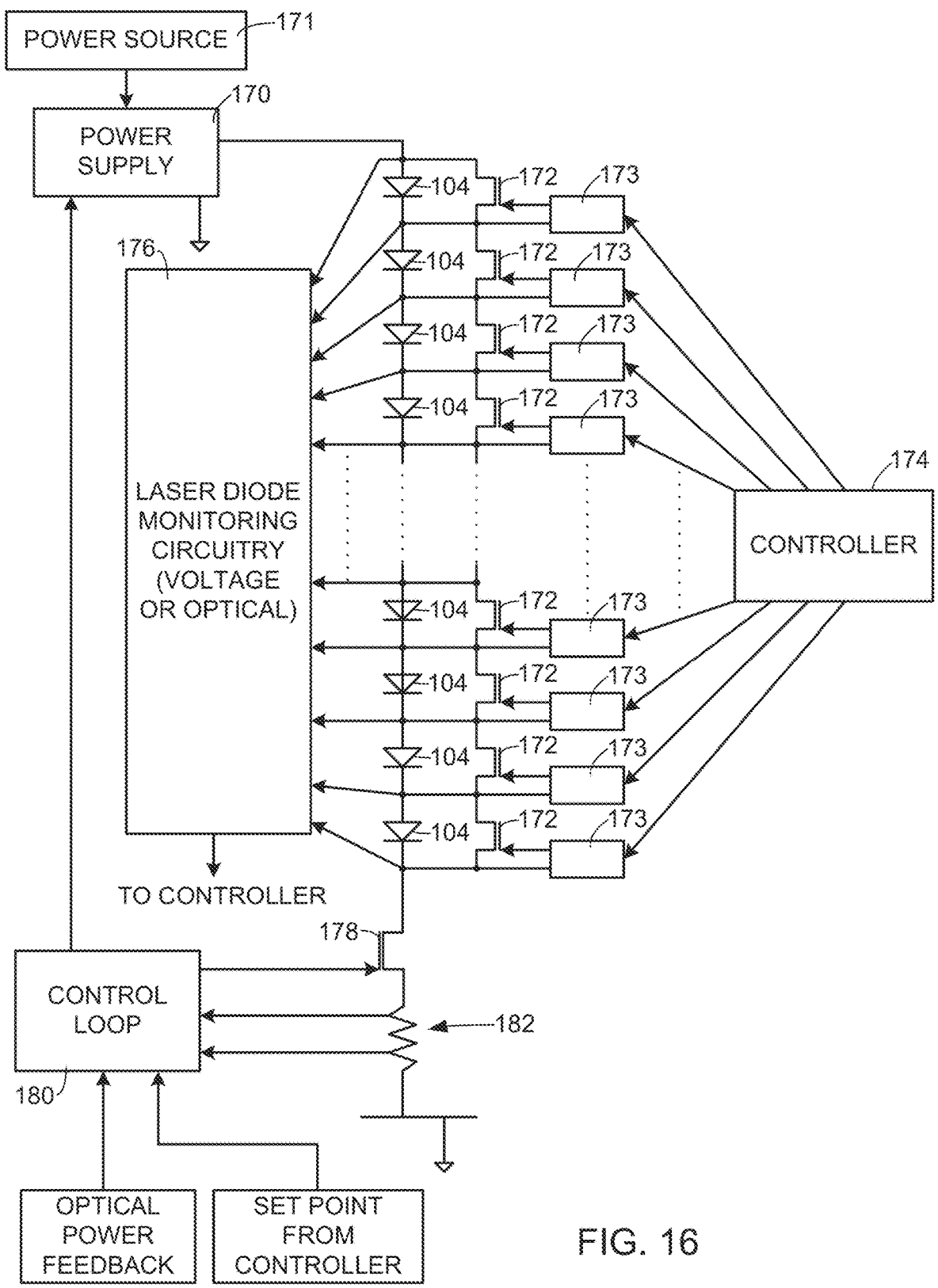
FIG. 16 is a simplified circuit diagram in accordance with embodiments of the invention.

FIG. 16 is a schematic diagram of an exemplary circuit used to facilitate one or more embodiments of the system 100 described above. In some embodiments, laser diodes 104 are arranged for individual or group activation by coupling a current from a power supply 170, which receives power from a suitable power source 171, to the individual or group of laser diodes 104 by shorting out individual or groups (subsets) of laser diodes using appropriate switches 172 (e.g., MOSFETs) responsive to control signals from a controller 174 comprising one or more processors. In some embodiments, control circuits 173 for the MOSFETs or switches 172, such as opto isolators, may be used to process the control signals from the controller 174.

In some embodiments, monitoring circuitry 176 is provided to monitor the performance of each of the laser diodes 104 either optically or by measuring a voltage drop across the diodes 104. This enables defective laser diodes 104 to be detected and isolated. In some embodiments, the circuitry 176 measures a voltage drop across the individual laser diodes 104 or a group of laser diodes 104 as feedback for the performance of the laser diodes 104.

In some embodiments, the circuitry includes a switch 178 (e.g., a MOSFET) that is configured to enable or disable current through the set of laser diodes 104.

In some embodiments, the system 100 includes control loop circuitry 180 for controlling the power supply 170. In some embodiments, the control loop circuitry 180 receives a voltage drop across a current sense resistor 182, such as a 4-terminal or a 2-terminal resistor, which is used to determine the current through the activated laser diodes 104. In some embodiments, the control loop circuitry 180 includes an optical power feedback, which indicates the intensity or power of the laser energy 102 delivered to a target. In some embodiments, the control loop circuitry 180 includes a set point from the controller 174 which indicates a desired power setting.

Some embodiments of the invention are directed to a method of producing a laser beam 102 using a laser system 100 in accordance with one or more embodiments described herein. In some embodiments of the method, a discreet beam of laser energy 106 is output from each of a plurality of laser diodes 104 of the system 100. A proximal end 112 of a fiber bundle 108 is optically coupled to the discreet beams of laser energy 106. The discreet beams of laser energy 106 are discharged through a distal end 120 of the fiber bundle 108 (laser energy 118). A proximal end 116 of a delivery fiber 114 is optically coupled to the discreet beams of laser energy 106 discharged through the distal end 120 of the fiber bundle 108. A composite beam of laser energy 102 comprising the discreet beams of laser energy 106 is discharged through a distal end 122 of the delivery fiber 114, which is optically-coupled to the fiber bundle 108.

In some embodiments, outputting or generating the discreet beams of laser energy 106 from each of a plurality of the laser diodes 104 of the system 100 comprises outputting a beam of laser energy 106 from a first subset of the laser diodes 104.

In some embodiments, the intensity of the composite beam 102 is adjusted by outputting or generating discreet beams of laser energy 106 from a second subset of the laser diodes 104 that is different from the first subset of the laser diodes 104. In accordance with this step of the method, the total number of laser diodes 104 that are activated by the system 100 to generate the discreet beams of laser energy 106 may be either increased or decreased to adjust the total power level of the composite beam of laser energy 102 discharged from the delivery fiber 114. This embodiment allows the surgeon to transition the laser energy 102 between high and low intensity modes, such as from a coagulation mode to a vaporization or cutting mode, or from an aiming beam mode, in which the laser energy 102 lacks sufficient intensity to damage tissue of the patient, to an active mode, in which the laser energy 102 has sufficient intensity to cut, vaporize or perform another laser procedure on tissue of the patient.

In some embodiments of the method, a wavelength or wavelengths of the composite beam of laser energy 102 is adjusted by outputting or generating discreet beams of energy 106 from a second set of laser diodes that is different from the first subset. In this embodiment, the first laser diode subset may produce a composite beam of laser energy 102 spanning a first set of wavelengths, whereas activation of the second laser diode subset results in a composite laser beam 102 spanning a different set of wavelengths. This embodiment allows the surgeon to transition the laser energy 102 between wavelengths that are useful for one type of laser procedure, to wavelengths that are useful in performing another type of laser procedure, for example. For instance, some wavelengths of the laser energy 102 are useful in vaporizing tissue (e.g., 532 nm), while other wavelengths of the laser energy 102 may be more useful in ablating or cutting tissue.

In some embodiments of the method, a size of the composite laser beam 102 is adjusted by outputting discreet beams of laser energy 106 from the second subset of the laser diodes 104 that is different from the first laser diode subset. As discussed above with reference to FIGS. 3 and 4, this allows the laser system 100 to adjust to the diameter of the composite laser beam 102. Additional techniques for adjusting the size and shape of the composite laser beam 102 discharged from the delivery fiber 114 involve selecting a delivery fiber 114 having an optical fiber that results in the desired size and shape of the discharge composite laser beam 102.

In some embodiments of the method, a shape of the composite laser beam 102 is adjusted by outputting discreet beams of laser energy 106 from a second subset of the laser diodes 104 that is different from the first laser diode subset. For example, a composite beam 102 having a shape of a circle (FIGS. 3 and 4), a ring (FIGS. 8-10), a line (FIGS. 5-7), a square, a rectangle, and concentric rings or circles (FIGS. 11-13), or other desired shape for the composite laser beam 102 may be realized through the selected activation and deactivation of subsets of the laser diodes 104.

In some embodiments of the method, a pattern of the composite laser beam 102 can be adjusted by outputting discreet beams of laser energy 106 from a second subset of the laser didoes that is different from the first laser diode subset. As discussed above, this may involve a periodic variation to the laser energy 106 discharged from the laser diodes 104 of the first laser diode subset as compared to the laser diodes 104 of the second laser diode subset.

In some embodiments of the method, the proximal end 112 of the fiber bundle 108 is optically coupled to the discreet beams of laser energy 106 by optically coupling the proximal end 112 of the fiber bundle 108 to the discreet beams of laser energy 106 using optics 124 comprising one or more lenses. In some embodiments of the method, the discreet beams of laser energy 106 are discharged through the distal end 120 of one or more of the optical fibers 110 of the fiber bundle 108.

In some embodiments of the method, optically coupling a proximal end 116 of the delivery fiber 114 to the discreet beams of laser energy 106 (laser energy 118) discharged through the distal end 120 of the fiber bundle 108 comprises optically coupling proximal end 116 of the delivery fiber 114 to the discreet beams of laser energy 106 discharged through the distal end 120 of the fiber bundle 108 using optics 150 comprising one or more lenses 152.

In some embodiments of the method, outputting a discreet beam of laser energy 106 from each of a plurality of the laser diodes 104 of the system 100 comprises outputting one or more discreet beams of excitation laser energy 106 having a wavelength within an excitation spectrum. In some embodiments, the method includes outputting one or more discreet beams of laser energy 106 having a wavelength within the excitation spectrum. In some embodiments, one or more of the discreet beams of laser energy 106 are passed through a filter 154 that filters one or more of the discreet beams of laser energy 106 such that they are within the excitation spectrum. In some embodiments, the excitation spectrum is 300-420 nanometers.

In some embodiments of the method, feedback electromagnetic energy 158 is transmitted from the distal end 122 of the delivery fiber 114 through the delivery fiber 114 and the fiber bundle 108 responsive to the exposure of tissue or a substance to the excitation laser energy. In some embodiments, the feedback electromagnetic energy 158 is delivered to a spectrometer 156 (FIG. 1). In some embodiments, the feedback electromagnetic energy 158 is filtered using a filter 160 before the feedback electromagnetic energy 158 is delivered to the spectrometer 156.

Figure 17:
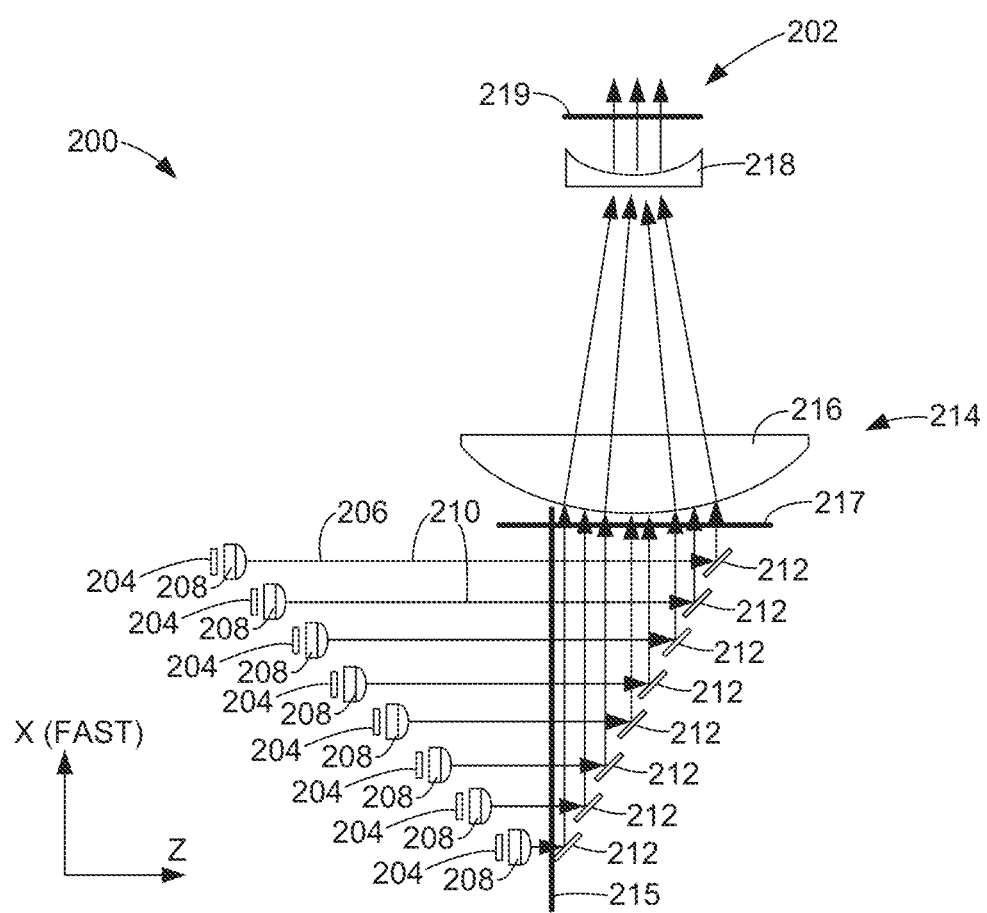
FIG. 17 is a simplified diagram of a portion of a laser bar, in which the slow axes of the laser diodes are aligned, in accordance with embodiments of the invention.
Figure 21:
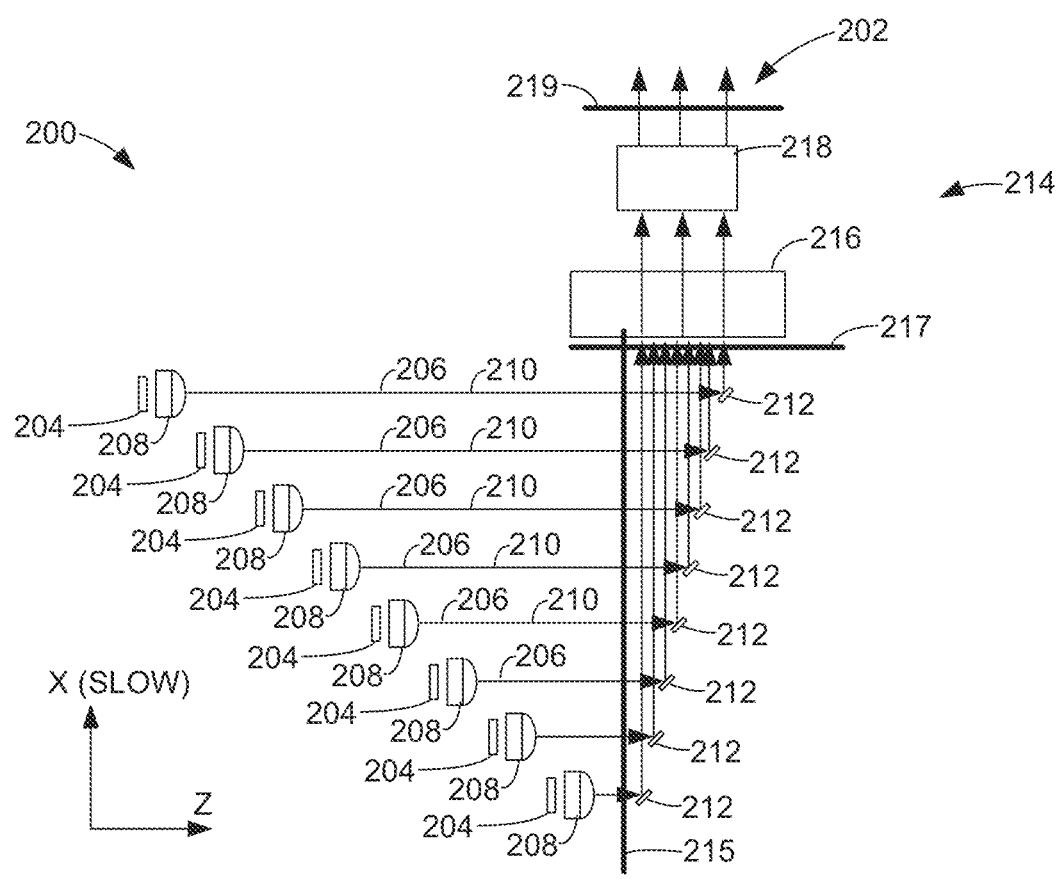
FIG. 21 is a simplified diagram of a laser bar, in which the slow axes of the laser diodes are aligned, in accordance with embodiments of the invention.

FIGS. 17 and 21 are simplified diagrams of laser bars 200 in accordance with embodiments of the invention. The laser bars 200 are configured to discharge a composite beam of laser energy 202 that is formed from laser energy discharged from a plurality of laser diodes 204. In some embodiments, the laser bar 200 includes a plurality of collimating lenses 208, each of which is configured to collimate the laser energy 206 output from one of the laser diodes 204 into a collimated beam of laser energy 210. In some embodiments, the collimating lenses 208 are aspheric lenses having a larger numerical aperture (NA>0.6).

In some embodiments, the laser bar 200 includes at least one mirror 212 configured to reflect the collimated beams 210. In some embodiments, the laser bar 200 includes optics 214 configured to gather the reflected collimated beams 210 into the composite beam 202, which may be discharged from the laser bar 200 to an optical fiber for delivery to a target. In some embodiments, the at least one mirror 212 comprises an individual mirror for each laser diode 204 that is configured to reflect the corresponding collimated beam 210 toward the optics 214, as shown in FIGS. 17 and 21. In some embodiments, each of the mirrors 212 are angled at approximately 45 degrees to the corresponding collimated beam 210.

In some embodiments, the spacing between each laser diode 204 in the X direction (as identified in the figures) is made as small as possible and is generally determined by the package of the laser diode 204. In some embodiments, the package for each laser diode 204 has a diameter of approximately 5.6 millimeters and the spacing along the X axis between individual laser diodes 204 is approximately 6 millimeters.

In some embodiments, the laser diodes 204 and their corresponding mirrors 212 are positioned such that the laser energy 206 discharged from each of the laser diodes 204 travels approximately the same total distance from the laser diodes 204 to the optics 214. In some embodiments, the mirrors 212 are displaced from the laser diodes 204 along the Z axis, and the mirrors 212 are displaced from the optics 214 along the X axis that is perpendicular to the Z axis, as shown in FIGS. 17 and 21.

In some embodiments, the laser energy output from the laser diodes 204 is asymmetrical. In some embodiments, the beam shape of the laser energy 206 discharged from each laser diode 204 is elliptical, as the fast axis along the pn junction has a much larger divergent angle compared to the slow axis, which is perpendicular to the pn junction.

Figure 18:
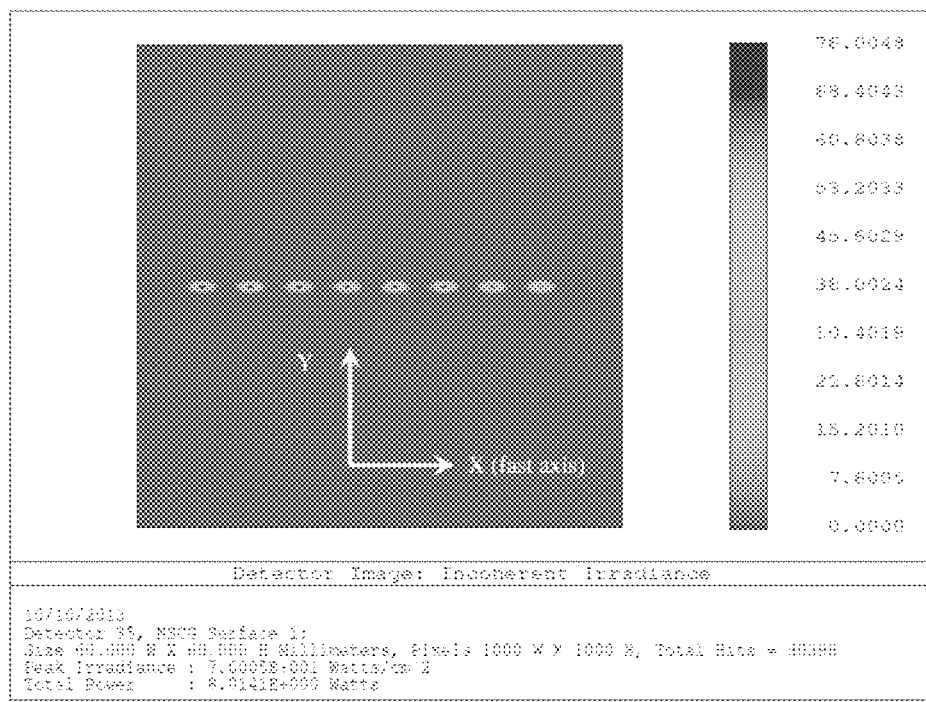
FIG. 18 illustrates exemplary profiles of laser energy beams at surface 1 of FIG. 17.
Figure 19:
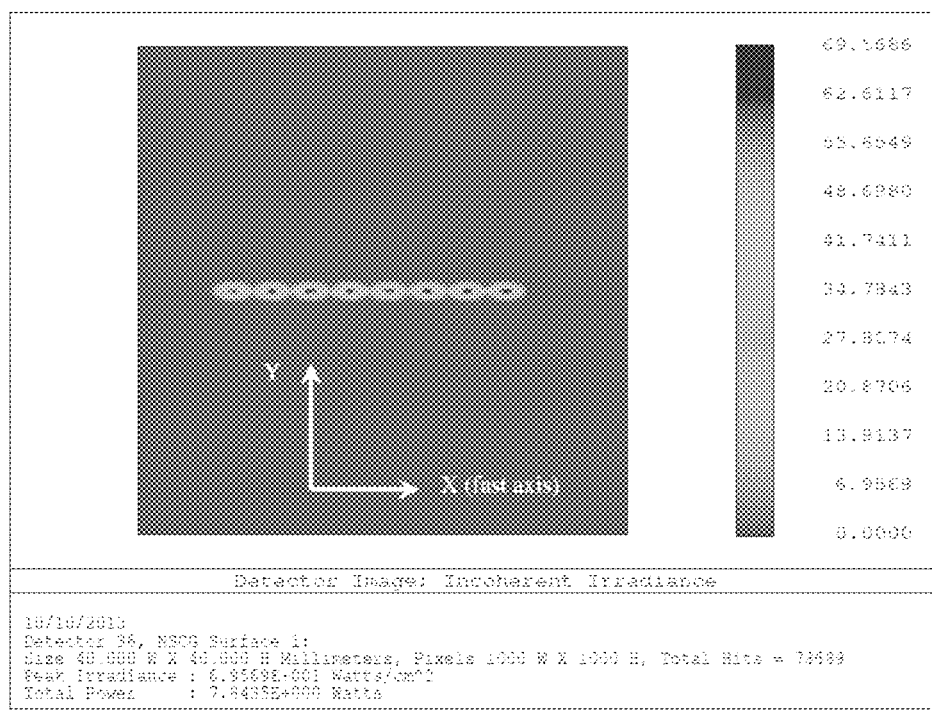
FIG. 19 illustrates exemplary profiles of laser energy beams at surface 2 of FIG. 17.

In some embodiments, the fast axes of the laser diodes are aligned in the X-Z plane, as shown in FIG. 17, and the laser energy 206 output from each of the laser diodes 204 and the corresponding collimated beams 210 are substantially aligned in the X-Z plane. This results in an elliptical beam profile at surface 215, as shown in FIG. 18, which is a simulation of the beam profiles produced using the ZEMAX software. The beam profiles at surface 217 of FIG. 17 are illustrated in FIG. 19.

Figure 22:
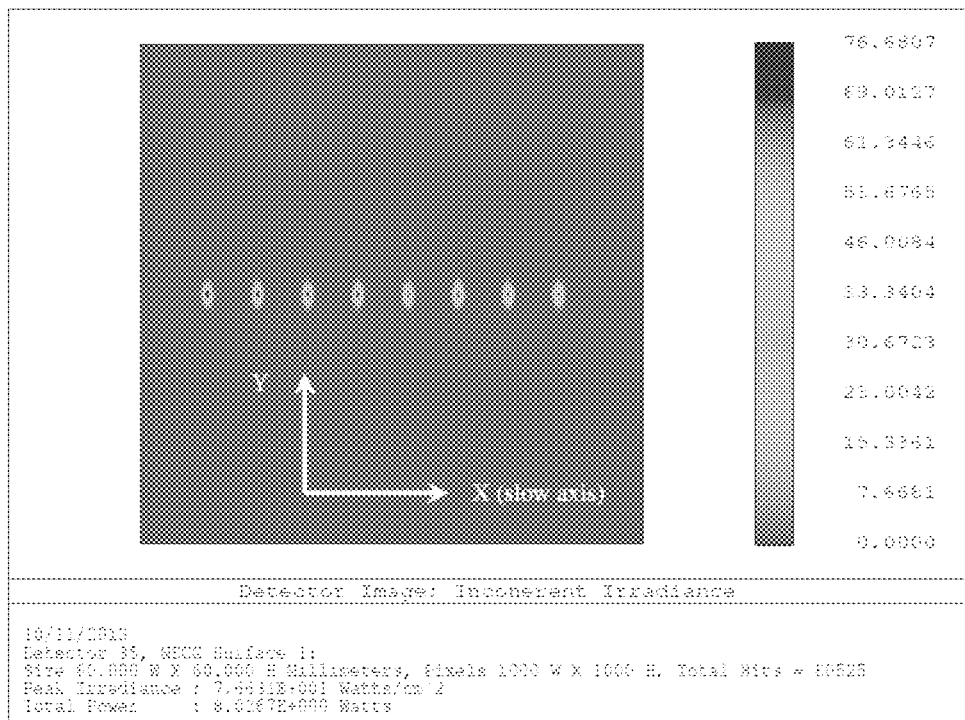
FIG. 22 illustrates laser energy beam profiles at surface 1 of FIG. 21.
Figure 23:
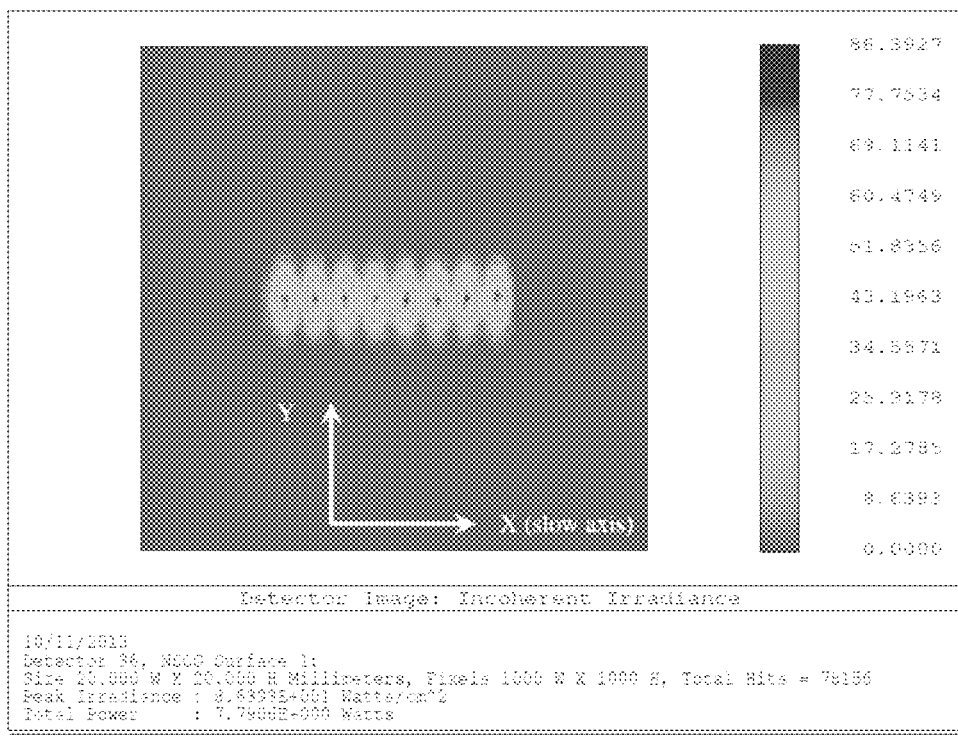
FIG. 23 illustrates exemplary profiles of laser energy beams at surface 2 of FIG. 21.

In some embodiments, the slow axes of the laser diodes 204 are aligned in the X-Z plane, as shown in FIG. 21, and the laser energy 206 and the corresponding collimated beams 210 are substantially aligned in the X-Z plane. This results in the beam profiles shown in FIG. 22 at surface 215, and the beam profiles shown in FIG. 23 at surface 217.

Figure 20:
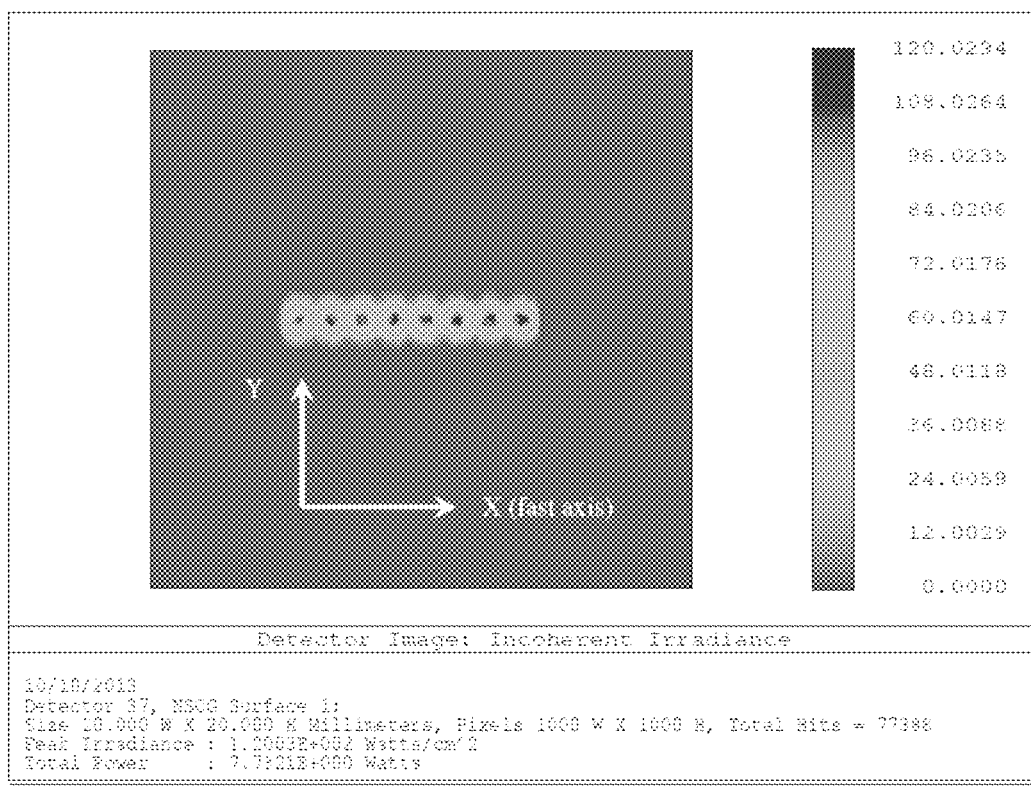
FIG. 20 illustrates exemplary laser energy beam profiles at surface 3 of FIG. 17.
Figure 24:
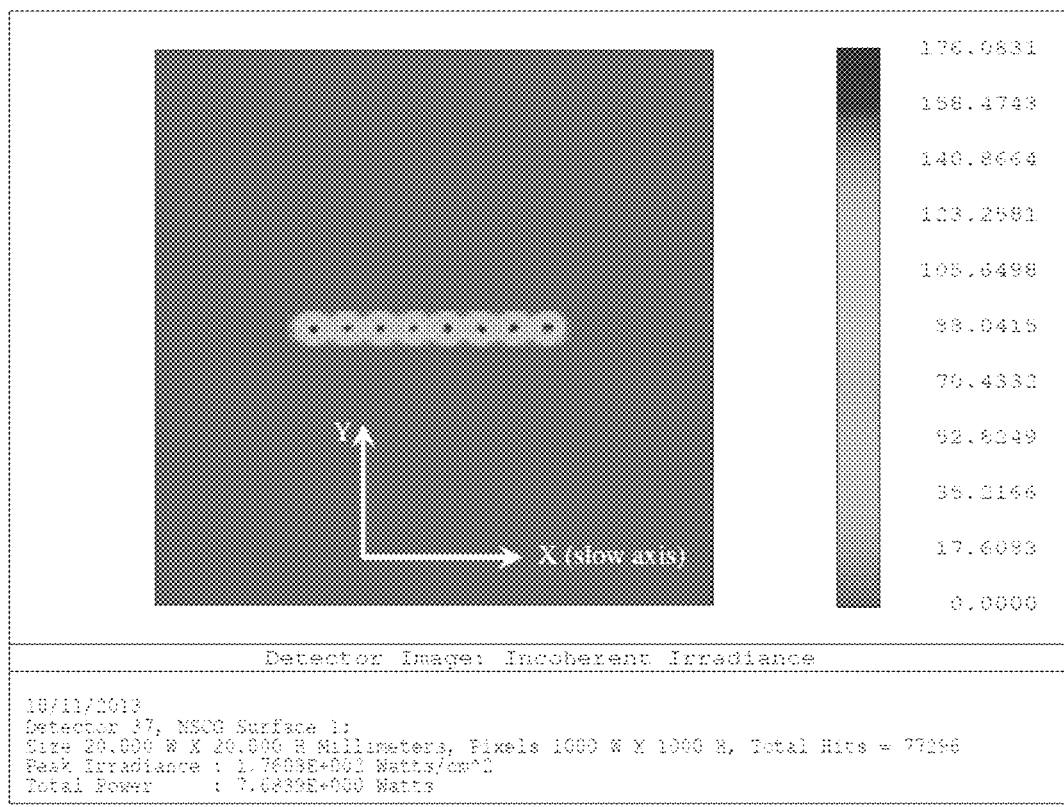
FIG. 24 illustrates exemplary profiles of laser energy beams at surface 3 of FIG. 21.

In some embodiments, the light combining optics 214 operate to reduce asymmetry of the collimated beams 210 reflected from the mirrors 212. In some embodiments, the light combining optics 214 include cylindrical lenses 216 and 218, which operate to reduce the fast axis beam divergent angle of each beam 210 and make it the same as the slow axis beam divergent angle. As a result, the individual beams output from the beam gathering optics 214 at surface 219 have substantially circular profiles, as shown in FIG. 20 (beam profiles at surface 219 of FIG. 17) and FIG. 24 (beam profiles at surface 219 of FIG. 21).

Figure 25:
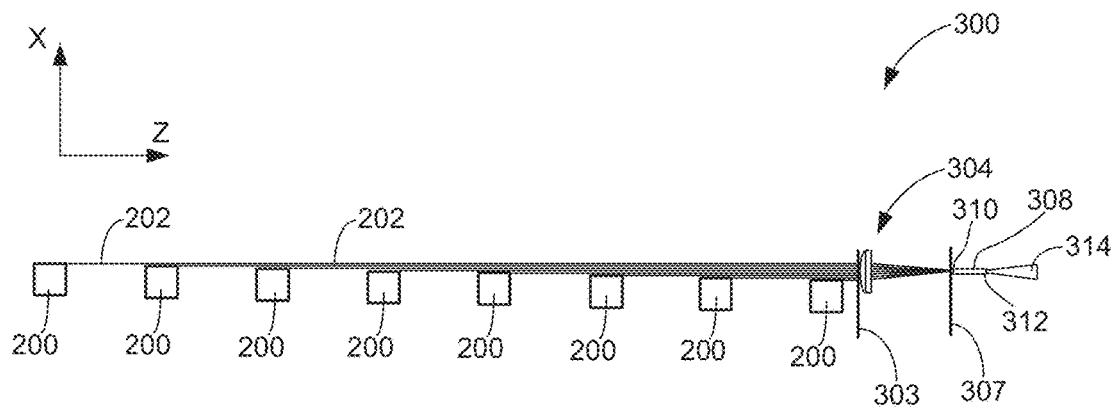
FIGS. 25 and 26 show simplified side and top views, respectively, of a laser module in accordance with embodiments of the invention.
Figure 26:
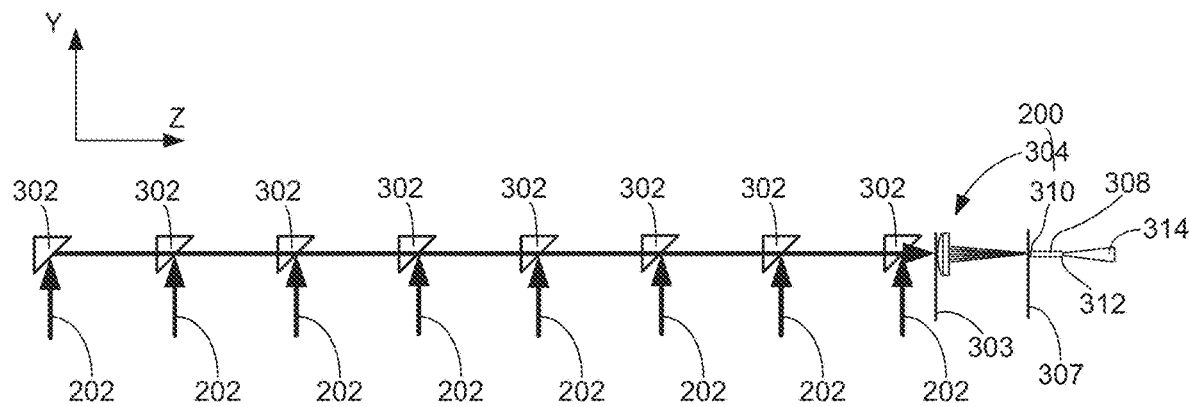

Some embodiments of the invention are directed to a laser module comprising two or more of the laser bars 200 formed in accordance with one or more of the embodiments described herein. FIGS. 25 and 26 show simplified side and top views, respectively, of an exemplary laser module 300 in accordance with embodiments of the invention, which includes eight laser bars 200. However, embodiments of the invention include laser modules 300 having more or fewer laser bars 200.

Figure 27:
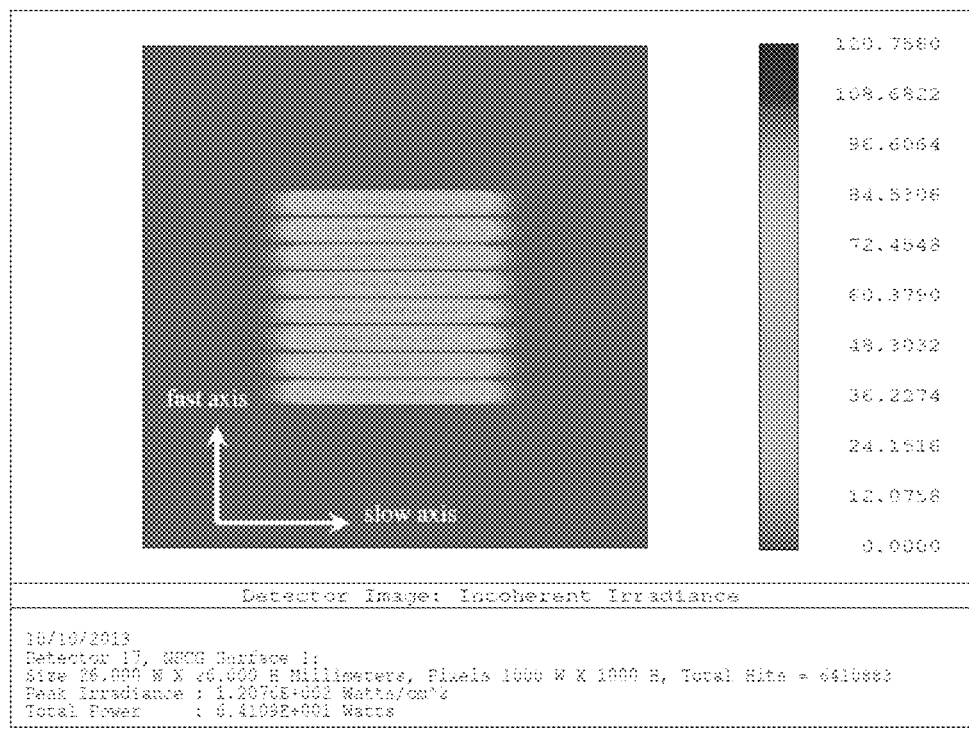
FIG. 27 illustrates an exemplary profile of the laser energy at surface 1 of FIGS. 25 and 26.

In some embodiments, the laser module 300 includes at least one mirror 302 that is configured to reflect the composite beams 202 of the laser bars 200. An exemplary profile of the reflected composite beams 202 of each beam bar 200 at surface 303 of FIGS. 25 and 26 is shown in FIG. 27. In some embodiments, the at least one mirror 302 comprises a plurality of mirrors 302 that are each configured to reflect one of the composite beams 202, as shown in FIG. 26. In some embodiments, each of the mirrors 302 is angled at approximately 45 degrees to their corresponding composite beam 202. In some embodiments, the optical distance of each laser bar 200 and the corresponding mirror 302 is optimized so that the optical distance from each laser bar 200 to surface 303 is the same.

In some embodiments, each of the mirrors 302 is displaced relative to the other mirrors 302 in the X direction. Preferably, this height difference of each of the mirrors 302 is as small as possible and is generally determined by the diameter of the bars 200. In some embodiments, each of the laser bars 200 has a diameter of approximately 1.2 millimeters, and the mirrors 302 are separated from each other in the X direction by approximately 1.4 millimeters.

Figure 28:
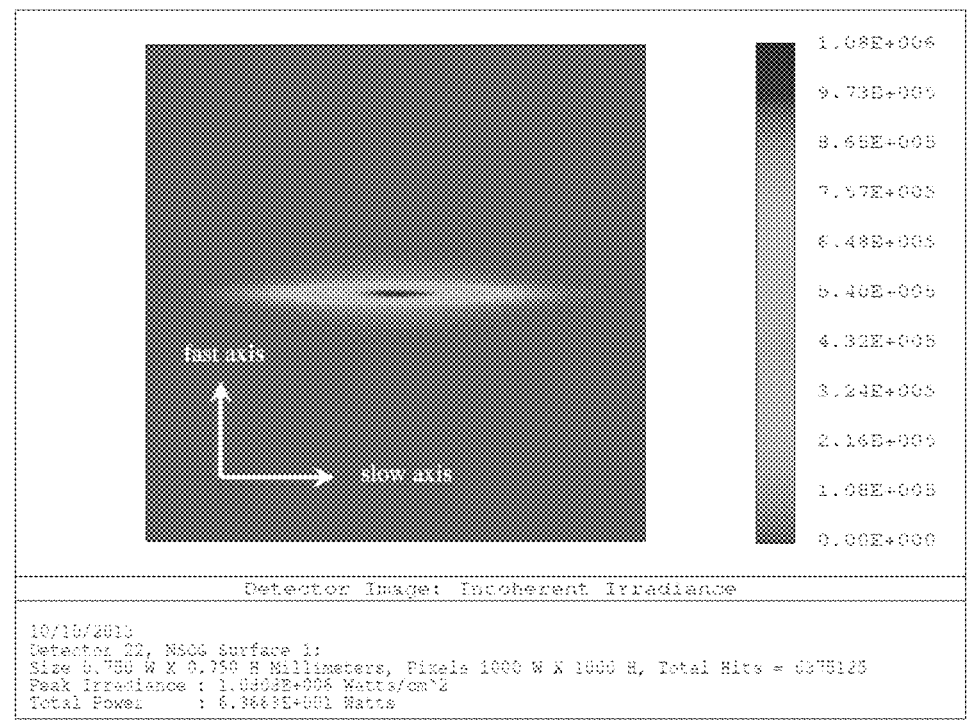
FIG. 28 illustrates an exemplary profile of the laser energy at surface 2 of FIGS. 25 and 26.

In some embodiments, the laser module 300 includes light focusing optics 304 configured to focus the reflected composite beams 202 into a convergent beam 306. In some embodiments, the light focusing optics 304 comprises a single spherical lens, as indicated in FIGS. 25 and 26. The resultant profile of the convergent beam 306 at surface 307 is shown in FIG. 28. The profile of the convergent beam 306 is elliptical after the spherical focusing lens 304 due to the wider dispersion angle of the laser energy along the fast axis of the beam 102 as compared to that along the slow axis.

In some embodiments, the laser module 300 includes an optical fiber 308 having a proximal end 310 optically coupled to the convergent beam 306. The optical fiber 308 may operate similarly to the delivery fibers 114 described above, and includes a distal end 312 through which the convergent beam 306 is discharged. The distal ends of the delivery fibers disclosed herein may have an end-firing configuration or a side-firing configuration (i.e., a beveled distal end), depending of the laser treatment/procedure being performed.

Figure 29:
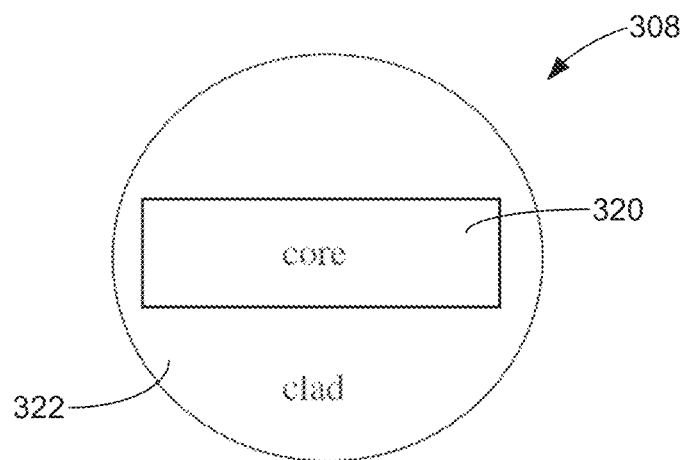
FIG. 29 is a simplified cross-sectional view of an optical fiber having a rectangular core, in accordance with embodiments of the invention.
Figure 30:
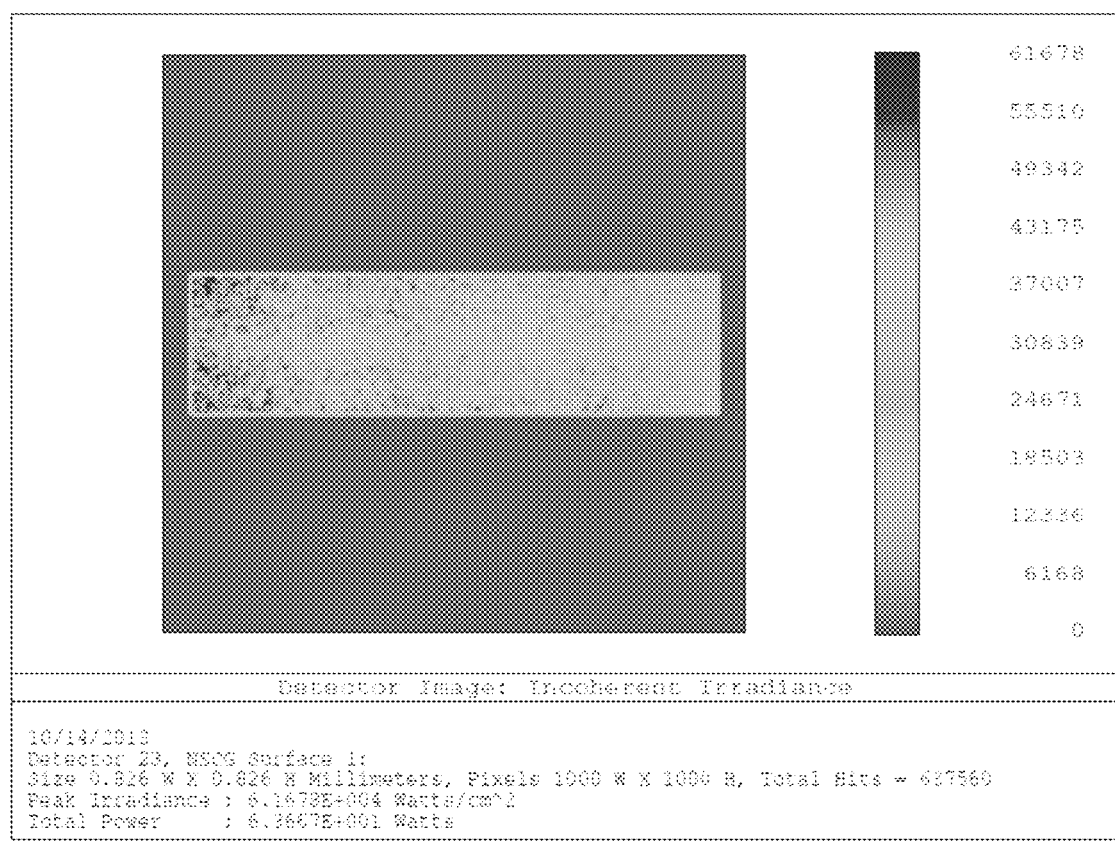
FIG. 30 illustrates an exemplary profile of laser energy discharged from the optical fiber of FIG. 29.

In some embodiments, the optical fiber 308 has a rectangular core 320 surrounded by cladding 322, as shown in the simplified cross-sectional view of FIG. 29. Such an optical fiber 308 can be used to deliver the elliptically shaped convergent beam 306 at the proximal end 310 of the fiber 308, which can be discharged from the delivery end of the optical fiber 308. In some embodiments, the rectangular core 320 has dimensions of 750 µm by 200 µm. An exemplary profile of the beam discharged from the optical fiber 308 having the rectangular core 320 is shown in FIG. 30. Such a rectangular or line shaped beam can behave like an optical knife for tissue cutting. Furthermore, by sweeping the line shaped beam, it can be used to vaporize tissues.

Figure 31:
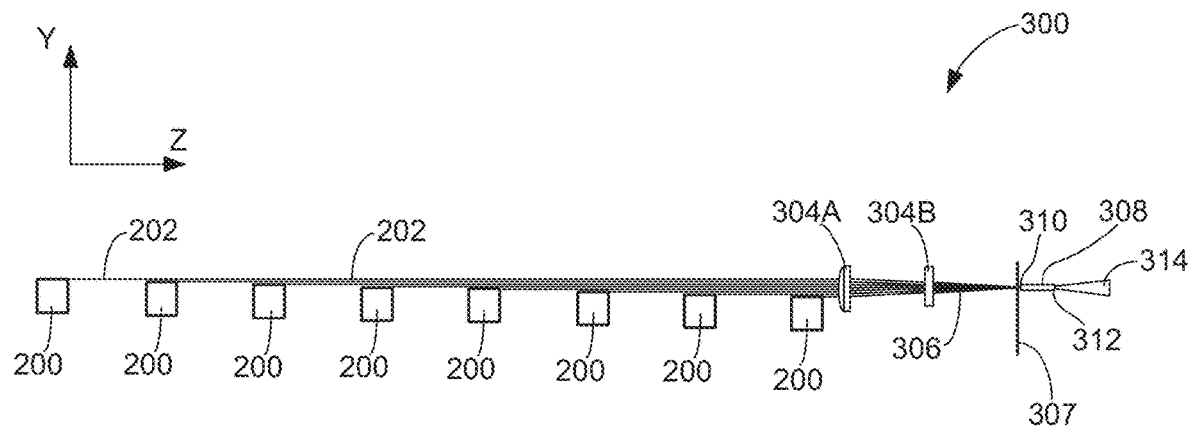
FIG. 31 is an exemplary laser module in accordance with embodiments of the invention.
Figure 32:
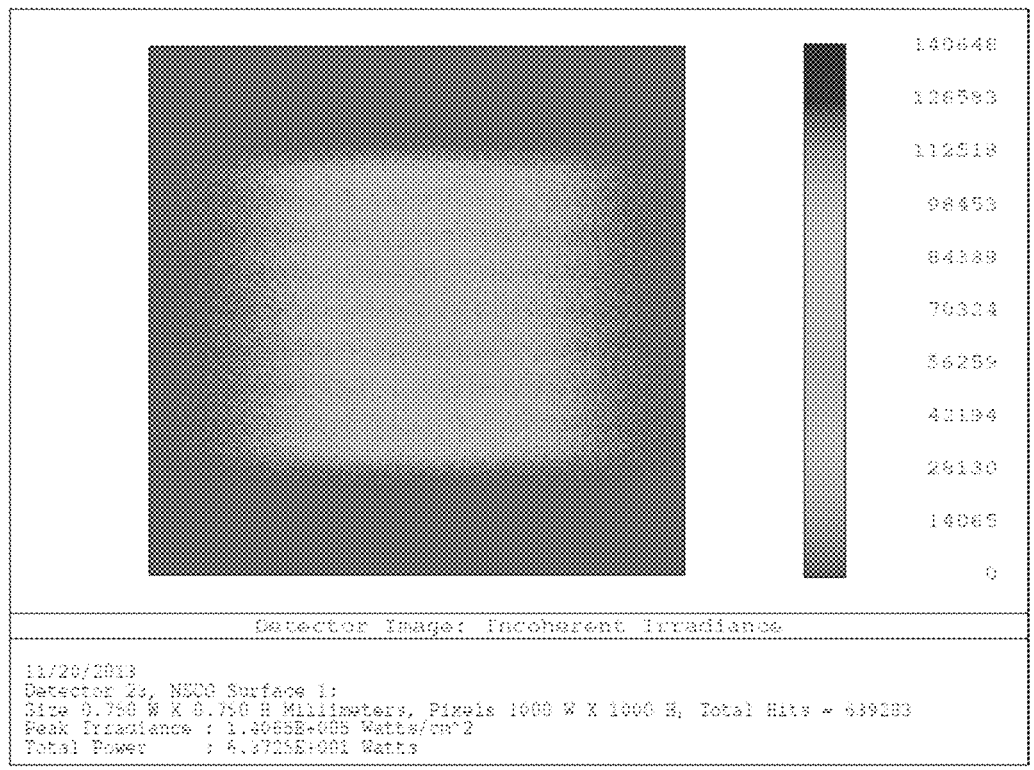
FIG. 32 illustrates an exemplary profile of laser energy at surface 2 of the system of FIG. 31.

In some embodiments, as depicted in FIG. 31, the light focusing optics 304 comprise two cylindrical lenses 304A and 304B to increase the launching beam area in front of the receiving fiber 308, and to make the beam 306 substantially square or rectangular in shape. An exemplary profile of the beam 306 at surface 307 of FIG. 31 is shown in FIG. 32. In some embodiments, a circular core shaped optical fiber 308 can be used to receive the beam 306 at the proximal end 310 and discharge a circular beam at the output end of the optical fiber 308.

Figure 33:
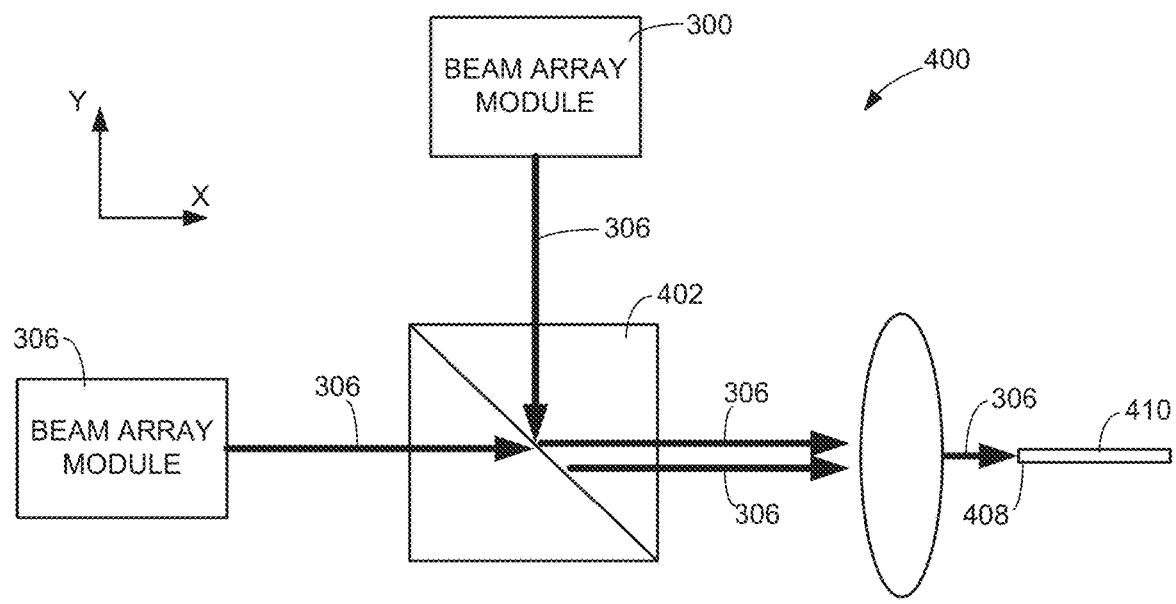
FIG. 33 is a simplified diagram of a laser system in accordance with embodiments of the invention.

Some embodiments of the invention are directed to a laser system 400, in which two or more of the laser modules 300 are combined. FIG. 33 is a simplified diagram of such a laser system 400 in accordance with embodiments of the invention. In some embodiments, the laser system 400 includes a polarization beam combining cube 402 that receives each of the composite output beams 306 from the modules 300 and outputs a composite beam 404 comprising each of the beams 306, as shown in FIG. 33. In some embodiments, one or more of the laser modules 300 are configured to output their beams 306 in the Y-direction, and one or more of the laser modules 300 are configured to output their beams 306 in the X-direction, as shown in FIG. 33.

In some embodiments, the X-direction beams 306 and the Y-direction beams 306 are linear-polarized beams with 90 degree polarization direction difference there-between. This can be implemented by having one set of the modules 300 using fast axis beam aligned bars 200 while the other group of modules 300 use slow axis beam aligned bars 200.

In some embodiments, the laser system 400 includes focusing optics 406, which are configured to couple the composite beam 404 to a proximal end 408 of an optical fiber 410, which can then discharge the beam 404 to a desired target.

Figure 34:
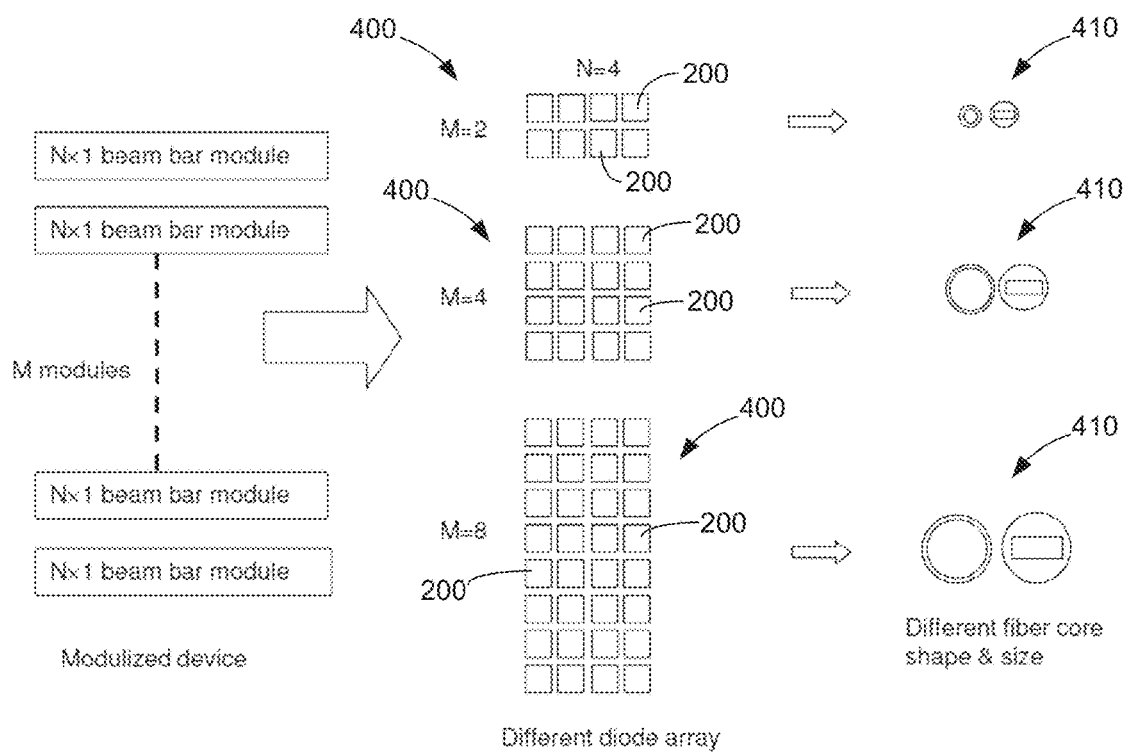
FIGS. 34 and 35 are simplified diagrams of laser systems in accordance with embodiments of the invention.
Figure 35:
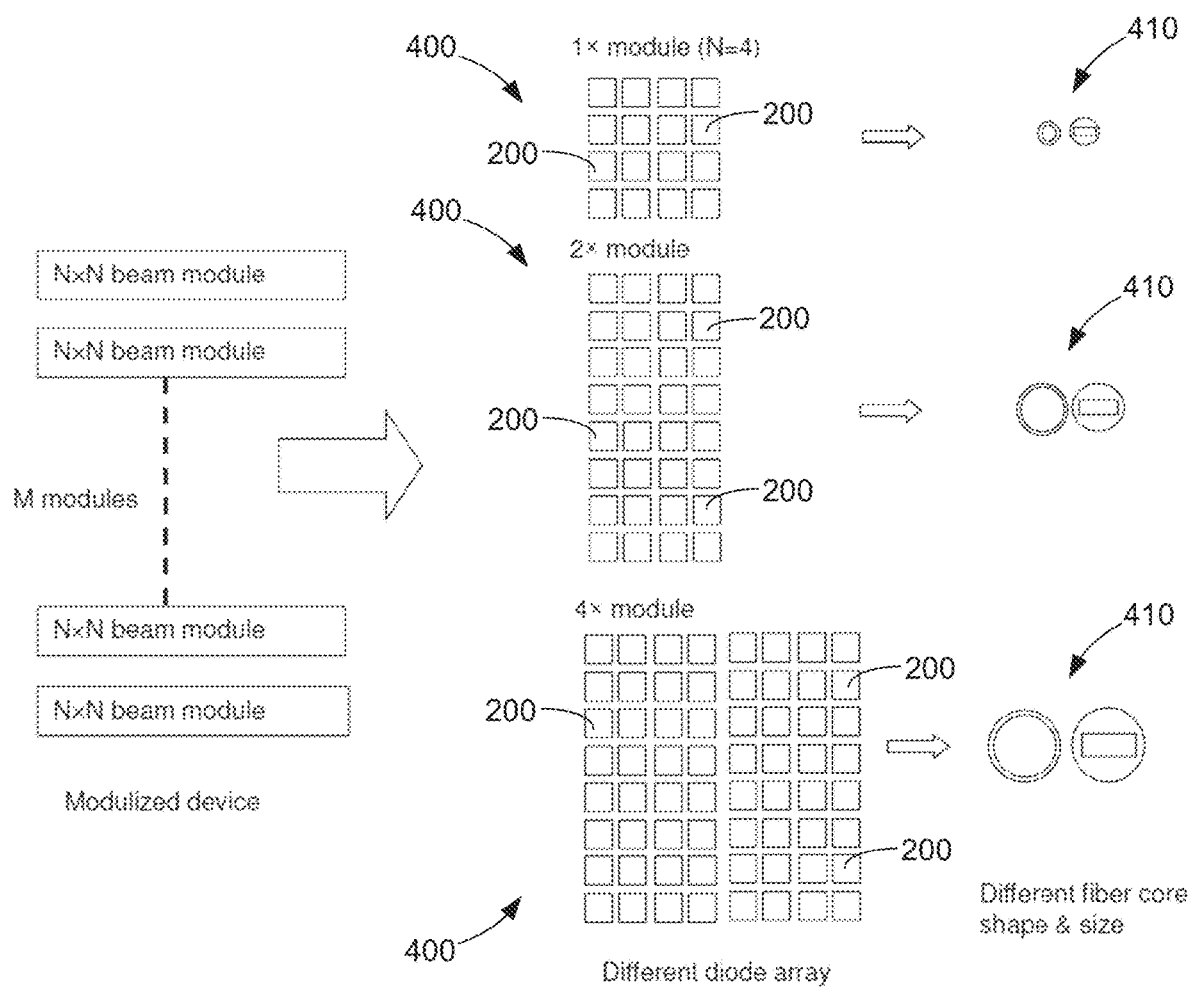

The free space optical beam combining achieved by the laser system 400 can be used to make a modularized device. Simplified diagrams of examples of such laser systems are illustrated in FIGS. 34 and 35. For example, as shown in FIG. 34, a beam array (M×N) can be formed using M sub-modules (each sub-module has an N×1 beam bar 200). To manufacture this system 400, a sub-module with N×1 beam bars 200 (where N is 2, 3, 4 . . . n) is made based on a customer's requirement, M sub-modules (where M is 1, 2, 3 . . . m) is plugged into the laser console to obtain the required output power (M×N times of single diode power). The power intensity is dependent on the output power and the delivery fiber core shape and size.

As shown in FIG. 35, another option is to make an N×N sub-module of the laser bars 200 and plug M of this module into a laser console based on output power requirements. The overall power is M×N×N times of a single laser diode power.

As mentioned above, the above-described laser systems and devices are useful generating and delivering laser energy that may be used to perform a surgical laser treatment on a patient. Exemplary surgical laser treatments include cutting, ablation, coagulation, lithotripsy, or other treatment. Embodiments of the invention include the performance of such surgical laser treatments on a patient using embodiments of the systems or devices described herein.

Although the present invention has been described with reference to preferred embodiments, workers skilled in the art will recognize that changes may be made in form and detail without departing from the spirit and scope of the invention.

What is claimed is:

1. A surgical laser system configured to deliver laser energy to tissue, the surgical laser system comprising:
    an array of laser diodes configured to output laser energy, including a first sub-array of laser diodes configured to deliver laser energy at a first wavelength range and a second sub-array of laser diodes configured to deliver laser energy at a second wavelength range;
    a fiber bundle, comprising a plurality of optical fibers, and including a proximal end optically coupled to the array of laser diodes and configured to receive the laser energy from the array of laser diodes; and
    a delivery fiber including a proximal end optically coupled to a distal end of the fiber bundle, wherein the delivery fiber has a rectangular core surrounded by a cladding and is configured to deliver the laser energy from the array of laser diodes as a rectangular or line shaped beam sufficient to perform laser surgery,
    wherein the plurality of optical fibers includes at least a first subset of optical fibers optically coupled to the first sub-array of laser diodes, and a second subset of optical fibers optically coupled to the second sub-array of laser diodes, and
    wherein the first subset of optical fibers are arranged consecutively in a first line and the second subset of optical fibers are arranged consecutively in one or more second lines, such that the first line and the one or more second lines are spaced apart from each other.

2. The surgical laser system according to claim 1, further comprising:
    circuitry configured to operate the first sub-array of laser diodes and the second sub-array of laser diodes independently.

3. The surgical laser system according to claim 1, wherein:
    the first sub-array of laser diodes and the second sub-array of laser diodes are configured and arranged in the system such that operation of the first sub-array results in a discharge of a first beam of laser energy, and
    simultaneous operation of the first and second sub-arrays results in a discharge of a second beam of laser energy having a different size or shape than the first beam.

4. The surgical laser system according to claim 3, wherein:
    the first subset of optical fibers and the second subset of optical fibers together form a rectangular core in cross-section, and
    a simultaneous discharge of energy from the first sub-array of laser diodes and the second sub-array of laser diodes generates an output beam with a rectangular cross-section.

5. The surgical laser system according to claim 1, further comprising:
    a user-actuated controller for operating the first sub-array of laser diodes and the second sub-array of laser diodes.

6. The surgical laser system according to claim 1, wherein at least one of the laser diodes in the array of laser diodes outputs a laser light with an output wavelength of 532 nm.

7. The surgical laser system according to claim 1, wherein each of the plurality of optical fibers of the fiber bundle is optically coupled to at least one of the laser diodes, and wherein the laser diodes are configured and arranged in the system so that a size of the laser energy discharged from the delivery fiber is adjustable through selective activation and deactivation of the laser diodes.

8. The surgical laser system according to claim 7, wherein at least one of the optical fibers is optically coupled to a plurality of the laser diodes of the array of laser diodes.

9. The surgical laser system according to claim 1, wherein:
    the first subset of optical fibers comprises optical fibers having fiber properties that are different than fiber properties of optical fibers of the second subset of optical fibers; and
    the fiber properties include one or more of a size of a core of an optical fiber from the optical fibers, a shape of the core of the optical fiber from the optical fibers, or a numerical aperture of the optical fiber from the optical fibers.

10. The surgical laser system according to claim 1, wherein the delivery fiber includes a multiple cladding fiber comprising:
    a central light delivery medium, wherein the cladding includes:
    a first cladding surrounding the rectangular core and having a first index of refraction;
    an annular light delivery medium surrounding the first cladding; and
    a second cladding surrounding the annular light delivery medium and having a second index of refraction.

11. The surgical laser system according to claim 10, wherein the laser energy discharged from the first sub-array of the laser diodes is optically coupled to the central light delivery medium, and the laser energy discharged from the second sub-array of the laser diodes is optically coupled to the annular light delivery medium.

12. The surgical laser system according to claim 10, wherein the first cladding is optically coupled to the first subset of optical fibers and the second cladding is optically coupled to the second subset of optical fibers to deliver the laser energy at a composite power to perform a surgical laser treatment.

13. The surgical laser system according to claim 1, wherein:
    the array of laser diodes includes an excitation laser diode configured to output excitation laser energy having a wavelength within an excitation spectrum, and
    the excitation laser diode is optically coupled to at least one of the optical fibers of the fiber bundle so that the fiber bundle is configured to deliver the excitation laser energy to a target via the delivery fiber.

14. The surgical laser system according to claim 1, wherein the first wavelength range and the second wavelength range are non-overlapping.

15. The surgical laser system according to claim 1, wherein the one or more second lines are parallel to one another, and wherein the first line is parallel to each of the one or more of the second lines.

16. A surgical laser system configured to deliver laser energy to tissue, the surgical laser system comprising:
    an array of laser diodes configured to output laser energy, including a first sub-array of laser diodes configured to deliver laser energy at first wavelength range and a second sub-array of laser diodes configured to deliver laser energy at a second wavelength range;
    a fiber bundle, comprising a plurality of optical fibers, and including a proximal end optically coupled to the array of laser diodes and configured to receive the laser energy from the array of laser diodes; and a delivery fiber including a proximal end optically coupled to a distal end of the fiber bundle, wherein the delivery fiber has a rectangular core surrounded by a cladding and is configured to deliver the laser energy from the array of laser diodes as a rectangular or line shaped beam sufficient to perform laser surgery, wherein the plurality of optical fibers includes at least a first subset of optical fibers optically coupled to the first sub-array of laser diodes, and a second subset of optical fibers optically coupled to the second sub-array of laser diodes, wherein at least two optical fibers from the first subset of optical fibers are arranged adjacent each other in a first linear orientation and at least two optical fibers from the second subset of optical fibers are arranged adjacent each other in a second linear orientation, and wherein a simultaneous discharge of laser energy from the first sub-array of laser diodes and the second sub-array of laser diodes generates an output beam with a rectangular cross-section.

17. A surgical laser system configured to deliver laser energy to tissue, the surgical laser system comprising:

an array of laser diodes configured to output laser energy, including a first sub-array of laser diodes configured to deliver laser energy at first wavelength range and a second sub-array of laser diodes configured to deliver laser energy at a second wavelength range;

a fiber bundle, comprising a plurality of optical fibers, and including a proximal end optically coupled to the array of laser diodes and configured to receive the laser energy from the array of laser diodes; and a delivery fiber including a proximal end optically coupled to a distal end of the fiber bundle, wherein the delivery fiber has a rectangular core surrounded by a cladding and is configured to deliver the laser energy from the array of laser diodes as a rectangular or line shaped beam sufficient to perform laser surgery, wherein the plurality of optical fibers includes at least a first subset of optical fibers optically coupled to the first sub-array of laser diodes, and a second subset of optical fibers optically coupled to the second sub-array of laser diodes, wherein the first subset of optical fibers are arranged in a first line such that at least two optical fibers from the first subset of optical fibers are adjacent each other, and the second subset of optical fibers are arranged in one or more second lines such that at least two optical fibers from the second subset of optical fibers are adjacent each other, such that the first line and the one or more second lines are spaced apart from each other, and wherein the first line and each of the one or more of the second lines are parallel to one another.

* * * * *